(12) United States Patent
Petersen

(10) Patent No.: US 7,972,789 B2
(45) Date of Patent: Jul. 5, 2011

(54) DYE COMPOUNDS

(75) Inventor: Kenneth H. Petersen, Smorum (DK)

(73) Assignee: Dako Denmark A/S, Glostrup (DK)

( * ) Notice: Subject to any disclaimer, the term of this patent is extended or adjusted under 35 U.S.C. 154(b) by 0 days.

(21) Appl. No.: 12/095,163

(22) PCT Filed: Nov. 24, 2006

(86) PCT No.: PCT/DK2006/000661
§ 371 (c)(1),
(2), (4) Date: Nov. 3, 2008

(87) PCT Pub. No.: WO2007/059779
PCT Pub. Date: May 31, 2007

(65) Prior Publication Data
US 2009/0136935 A1    May 28, 2009

Related U.S. Application Data

(60) Provisional application No. 60/740,074, filed on Nov. 28, 2005.

(51) Int. Cl.
*C12Q 1/68* (2006.01)
*C07D 221/18* (2006.01)
*C07H 21/00* (2006.01)
*C07H 21/02* (2006.01)

(52) U.S. Cl. ............ 435/6; 422/61; 536/24.3; 536/26.6; 546/26

(58) Field of Classification Search ..... 435/6; 536/24.3, 536/26.6; 422/61; 546/26
See application file for complete search history.

(56) References Cited

U.S. PATENT DOCUMENTS

| | | | |
|---|---|---|---|
| 5,268,486 | A | 12/1993 | Waggoner et al. |
| 5,486,616 | A | 1/1996 | Waggoner et al. |
| 5,569,587 | A | 10/1996 | Waggoner |
| 5,839,091 | A | 11/1998 | Rhett et al. |
| 5,948,359 | A | 9/1999 | Kalra et al. |
| 6,183,693 | B1 | 2/2001 | Bogen et al. |
| 6,352,861 | B1 | 3/2002 | Copeland et al. |
| 6,686,145 | B1 | 2/2004 | Waggoner et al. |

FOREIGN PATENT DOCUMENTS

| | | |
|---|---|---|
| EP | 0 747 700 A2 | 12/1996 |
| EP | 0 747 700 A3 | 12/1996 |
| EP | 0 747 448 B1 | 11/2002 |
| GB | 2 089 055 A | 6/1982 |

(Continued)

OTHER PUBLICATIONS

Stratagene (Catalog 1988, p. 39).*

(Continued)

*Primary Examiner* — Jezia Riley
(74) *Attorney, Agent, or Firm* — Finnegan, Henderson, Farabow, Garrett & Dunner, L.L.P.

(57) ABSTRACT

The present disclosure provides compounds that may be used as chromogens, fluorochromes, or as both. Said compounds may further be used as substrate for at least one enzyme, wherein said enzyme is capable of processing an aromatic amine group ($-NH_2$), an aromatic hydroxyl group ($-OH$), or an aromatic phosphate group ($-PO_4$). Furthermore, the present disclosure also provides methods for precipitating said compounds as well as methods for detecting a target using said compounds. Even further, kits comprising said compounds are disclosed. Said compounds may be used in any method utilizing a fluorochrome, a chromogen, or both.

39 Claims, 11 Drawing Sheets

Cyanine

Formula X

FOREIGN PATENT DOCUMENTS

| | | |
|---|---|---|
| WO | WO 00/75237 A2 | 12/2000 |
| WO | WO 2004/057307 A1 | 7/2004 |
| WO | WO 2004/057308 A1 | 7/2004 |
| WO | WO 2004/058404 A2 | 7/2004 |
| WO | WO 2004/058404 A3 | 7/2004 |
| WO | WO 2004/058950 A1 | 7/2004 |
| WO | WO 2004/059284 A2 | 7/2004 |
| WO | WO 2004/059284 A3 | 7/2004 |
| WO | WO 2004/059287 A2 | 7/2004 |
| WO | WO 2004/059287 A3 | 7/2004 |
| WO | WO 2004/059288 A2 | 7/2004 |
| WO | WO 2004/059288 A3 | 7/2004 |
| WO | WO 2004/059297 A1 | 7/2004 |
| WO | WO 2004/059441 A2 | 7/2004 |
| WO | WO 2004/059441 A3 | 7/2004 |
| WO | WO 2004/065491 A1 | 8/2004 |
| WO | WO 2007/059779 A3 | 5/2007 |

OTHER PUBLICATIONS

Ushomirskii et al. (Zhurnal Prikladnoi Spektroskopii (1984), 40(4),593-9). Abstract only.*

Beilstein Database Accession No. 3894857, XP-002403557, Al'perowitsch et al., *Zh. Obshch. Khim.*, 1959, vol. 29, pp. 989-994.

Beilstein Database Accession No. 3895448, XP-002403558, Al'perowitsch et al., *Zh. Obshch. Khim.*, 1959, vol. 29, pp. 989-994.

Beilstein Database Accession No. 3895599, XP-002403566, Al'perowitsch et al., *Zh. Obshch. Khim.*, 1959, vol. 29, pp. 989-994.

Beilstein Database Accession No. 4027742, XP-002403555, Lifshitz et al., *J. Gen. Chem. USSR* (Eng. Trans,), 1968, vol. 38, pp. 1965-1969.

Beilstein Database Accession No. 9087488, XP-002403569, Kabatc et al., *J. Chem. Soc. Perkin Trans. 2*, 2002, vol. 2, pp. 287-295.

Beilstein Database Accession No. 9091355, XP-002403571, Kabatc et al., *J. Chem. Soc. Perkin Trans. 2*, 2002, vol. 2, pp. 287-295.

Beilstein Database Accession No. 9092060, XP-002403572, Kabatc et al., *J. Chem. Soc. Perkin Trans. 2*, 2002, vol. 2, pp. 287-295.

Bystryak, S.M. et al., "Photochemical amplification for horseradish peroxidase-mediated immunosorbent assay," *Anal. Biochem.*, 1992, vol. 202, pp. 390-393.

Chao, J. et al., "Immunofluorescence signal amplification by the enzyme-catalyzed deposition of a fluorescent reporter substrate (CARD)," *Cytometry*, 1996, vol. 23, pp. 48-53.

Johnstone, A.P. and Turner, M.W., eds., *Immunochemistry 2-A Practical Approach*, Oxford University Press, 1997, pp. 71-130.

Kemeny, D.M., "Enzyme-linked immunoassays," pp. 147-175 in *Immunochemistry 1—A Practical Approach*, Johnstone, A.P. et al., IRL Press, 1997.

Moreau, M. et al., "Synthèse d'indomonocarbocyanines à elimination biliaire sélective: Étude expérimentale chez l'animal," *Eur. J. Med. Chem., Chimica Therapeutica*, 1974, vol. 9, No. 3, pp. 274-280.

Mujumdar, R.B. et al., "Cyanine dye labeling reagents containing isothiocyanate groups," *Cytometry*, 1989, vol. 10, pp. 11-19.

Noland, W.E. et al., "Nitration of indoles. III. Polynitration of 2-alkylindoles," *J. Am. Chem. Soc.*, 1990, vol. 30, pp. 3457-3469.

Pham, W. et al., "Synthesis and application of a water-soluble near-infrared dye for cancer detection using optical imaging," *Bioconjugate Chem.*, 2005, vol. 16, pp. 735-740.

Self, C.H., "Enzyme amplification—a general method applied to provide an immunoassisted assay for placental alkaline phosphatase," *J. Immunol. Methods*, 1985, vol. 76, pp. 389-393.

Shragina, L. et al., "Searching for photochromic liquid crystals: Spironaphthoxazine substituted with a mesogenic group," *Liquid Crystals*, 1990, vol. 7, pp. 643-655.

* cited by examiner

Cyanine

Formula X

Merocyanine

Formula XI

Styryl

Formula XII

Compound IIIa

Compound IVa

Compound IIIb

Compound VII

Figure 8a-f

DYE COMPOUNDS

This application is a national stage filing under 35 U.S.C. §371 of International Application No. PCT/DK2006/000661 filed on Nov. 24, 2006. This international application also claims the benefit of U.S. Provisional Patent Application No. 60/740,074, filed on Nov. 28, 2005. All of those applications are incorporated by reference herein.

TECHNICAL FIELD

This invention relates to compounds that may be used both as a chromogen and as a fluorochrome, as well as methods for detecting a target using said compounds.

BACKGROUND OF THE INVENTION

The detection and quantification of biological material, such as cells, proteins, e.g. cytokines and antibodies, drugs, nucleic acid, e.g. DNA and RNA, etc., using fluorescent labeling or enzyme-processed chromogens is widely applied in different biological assay systems.

The fluorescent dye is particularly useful for assays like immuno histochemistry (IHC), flow cytometry, fluorescent in situ hybridization (FISH) and similar systems. Fluorescent dyes, or fluorochromes, are fluorescent when appropriately excited under normal conditions of use chromogens have different characteristics than fluorochromes and form colored precipitates when processed by an enzyme. Under normal conditions of use chromogens form intensely colored precipitates when viewed using ordinary lighting conditions. Chromogens are frequently used in IHC, and similar enzyme-linked immuno assays.

Most enzyme-linked assays are based on one of the two enzymes alkaline phosphatase (AP), a hydrolase (Self C H, J Imm Methods 76:389-393, 1985) or horseradish peroxidase (HRP), an oxidoreductase (Bystryak, Mekler, Anal Biochem 202:390-393, 1992). Alkaline phosphatase activity is in general expressed through hydrolysis of a reporter substrate and its subsequent reaction with a diazonium salt to generate a detectable signal. HRP oxidizes a reporter substrate and this reporter substrate will then through polymerization or covalent attachment generate a detectable signal.

Cyanine dyes and related polymethine dyes are well known in the literature (Tyutyulkov, N., et al., *Polymethine dyes: Structure and properties*. 1st ed. 1991: St. Kliment Ohridski University press. 249). Furthermore, modifications of the dyes to provide desired solubility, reactivity and spectroscopic properties have also been suggested (Tyutyulkov, N., et al., *Polymethine dyes: Structure and properties*. 1st ed. 1991: St. Kliment Ohridski University press. 249).

Cyanine dyes as substrate for enzymes has been described previously, however only in systems where the dyes are coupled to a molecule that is known to be a substrate for an enzyme (in this case horse radish peroxidase (HRP)). Chao et al. (Cytometry 23:48-53, 1996) describes a fluorescent horse-radish peroxidase substrate Cy3.29-tyramide and its application in an enzyme-based signal amplification system (catalyzed reporter deposition, CARD).

EP 747 448 describes fluorescent monomethine rigidized dye compounds emitting near UV and blue (300-500 nm) region of the spectrum.

U.S. Pat. No. 6,686,145 describes fluorescent rigidized dye compounds capable of producing fluorescence in the green to orange region of the spectrum.

U.S. Pat. No. 5,268,486 describes cyanine and polymethine dyes developed with substituent groups which are covalently reactive with sulfhydryl groups, amine groups, and hydroxyl groups on proteins and other materials for purposes of fluorescence and phosphorescence detection of those materials.

U.S. Pat. No. 5,569,587 describes to labeling of proteins, DNA, drugs, blood cells, etc. with luminescent polymethine cyanine and polymethine dyes at an amine or hydroxyl site on those materials.

Complex analysis of biological material demands parallel analysis of several biological molecules to obtain the desired information. Today's assay systems are most often limited by the number of colors available to perform such analysis of several markers in different colors on one tissue section.

It is thus highly desirable to develop means and methods for more colors to be available in biological assays to allow for e.g. parallel analysis of biological markers and molecules, and to allow manipulation of the color of the dye to suit specific needs of the user, such as specific color needs or choice of fluorescence or visual detection systems, in an easy and simple way. In this respect the present invention addresses this need and interest.

SUMMARY OF THE INVENTION

In view of the above needs and interests regarding analysis of biological markers and molecules, particularly analysis of several markers in parallel in one sample such as on one tissue section, allowing for more colors of use in said assays, the present invention provides compounds that may be used both as excellent chromogens and fluorochromes.

One object with the present invention is to provide compounds according to Formulas X-XII as a chromogen, or as a fluorochrom, or as both.

The invention further provides uses of said compounds as a chromogen, or as a fluorochrom, or as both.

Also, the present invention provides uses of the compounds according to the invention as a substrate for at least one enzyme. The use may in further embodiments be wherein the at least one enzyme is capable of processing an aromatic amine group (—$NH_2$), an aromatic hydroxyl group (—OH), or an aromatic phosphate group (—$PO_4$).

Even further, said uses may be wherein the enzyme is conjugated to a binding molecule capable of binding to at least one target of interest.

In still even further embodiments, the at least one enzyme is HRP, or AP, or both.

In further embodiments,
  dotted lines $Z_1$ and $Z_2$ represents the atoms necessary to complete the formula selected from the groups consisting of one ring, two fused rings, and three fused rings each said ring having 4 or 5 or 6 carbon atoms and wherein at least one of said rings has at least one aromatic amine group (—$NH_2$), or at least one aromatic hydroxyl group (—OH), or at least one aromatic phosphate group (—$PO_4$), or a mixture thereof, attached,
  k and m and n are independently 1 or 0,
  $R_1$ through $R_{13}$ are individually selected from the group consisting of -D and —$(B)_i$-$(D)_j$,
  X and Y can independently be oxygen, sulfur, selenium, —$C(CH_3)_2$—, or —CH=CH—, and
  $A_1$ and $A_2$ are selected from the group consisting of -D and —(B)i-(D)j.
Some embodiments are where i and j independently are any numeral between 0-6, such as 0, 1, 2, 3, 4, 5, 6.
  In some embodiments, i is 1.
  In some further embodiments, j is 1.
  In still further embodiments i is 1 and j is 1.

In further embodiments, B is a linker. B may in further embodiments be selected from the group consisting of branched alkyl chains of 1-20 carbon atoms, such as 1, 2, 3, 4, 5, 6, 7, 8, 9, 10, 11, 12, 13, 14, 15, 16, 17, 18, 19, or even 20 carbon atoms, straight alkyl chains of 1-20 carbon atoms, such as 1, 2, 3, 4, 5, 6, 7, 8, 9, 10, 11, 12, 13, 14, 15, 16, 17, 18, 19, or even 20 carbon atoms, monoethers containing from 2-20 carbon atoms, such as such as 2, 3, 4, 5, 6, 7, 8, 9, 10, 11, 12, 13, 14, 15, 16, 17, 18, 19, or even 20 carbon atoms, polyethers containing from 2-20 carbon atoms, such as 2, 3, 4, 5, 6, 7, 8, 9, 10, 11, 12, 13, 14, 15, 16, 17, 18, 19, or even 20 carbon atoms, and polymethine chains containing from 1 to 6 carbon atoms, such as 1, 2, 3, 4, 5, or even 6 carbon atoms; and optionally B may connect two of the groups $A_1$, $A_2$, and/or $R_{1-7}$ forming an additional ring system between two of $A_1$, $A_2$, and $R_{1-7}$ thereby making the central methine chain part of a ring system.

The invention further provides a method for precipitating a compound according to the formulas

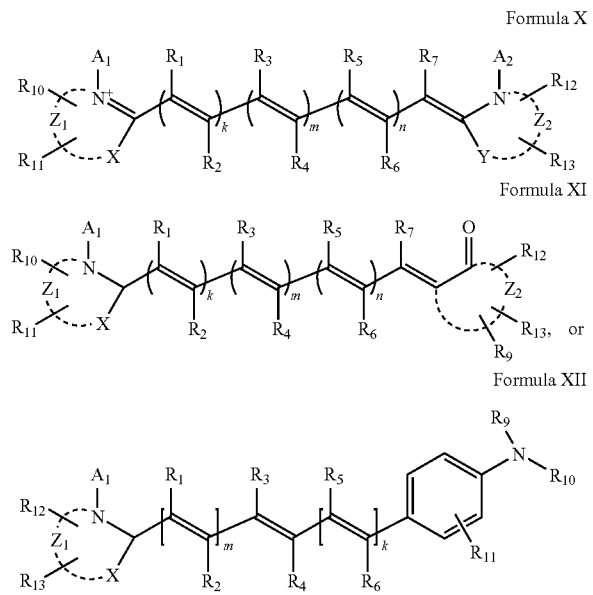

the method comprising the steps of
  a) providing said compound according to formula X, formula XI, or formula XII,
  b) providing an enzyme,
  c) contacting the compound according to the invention with said enzyme,
  d) optionally providing a co-factor,
wherein said compound forms a precipitate.

Further embodiments are wherein the method further comprises the step of detecting said precipitate.

In even further embodiments, the precipitate is detected by microscopy, e.g. light or fluorescence microscopy.

The invention further provides a method for detecting a target,
  the method comprising the steps of
  a) providing said at least one compound according to formula

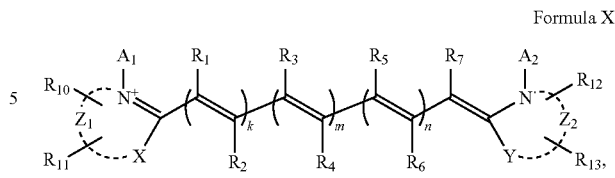

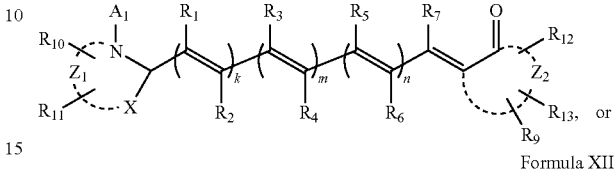

b) providing at least one enzyme,
  c) contacting the compound according to the invention with said enzyme,
  d) optionally providing a co-factor, and
  e) detecting said precipitate,
wherein the detection for said precipitate is a direct or indirect detection of said target.

In further embodiments, the precipitate is detected by microscopy, e.g. light microscopy, fluorescent microscopy, or both.

In further embodiments, the above methods may be histochemistry, immunohistochemistry, cytochemistry, immunocytochemistry, ELISA (enzyme linked immunosorbent assay), ISH (in situ hybridization), FISH (fluorescent in situ hybridization), CISH (chromogen in situ hybridization), flow cytometry, or any other method utilizing either a chromogenic compound, a fluorescens compound, or both.

In another embodiment, the above methods are immunohistochemistry, immunocytochemistry or CISH (chromogen in situ hybridization).

The invention further provides a compound according to formula

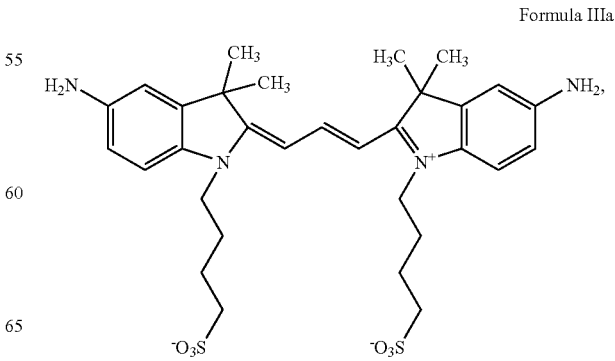

-continued

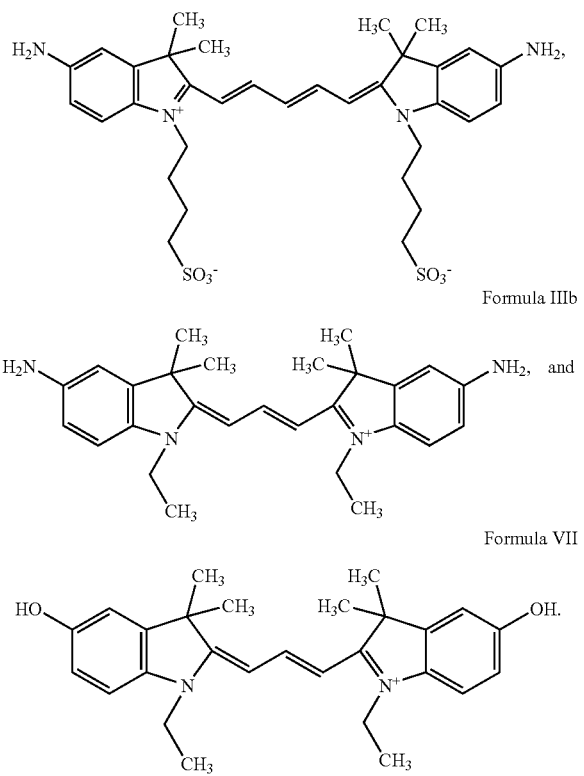

Formula IVa

Formula IIIb

Formula VII

Still even further, the invention discloses a kit comprising a) at least one compound according to formula

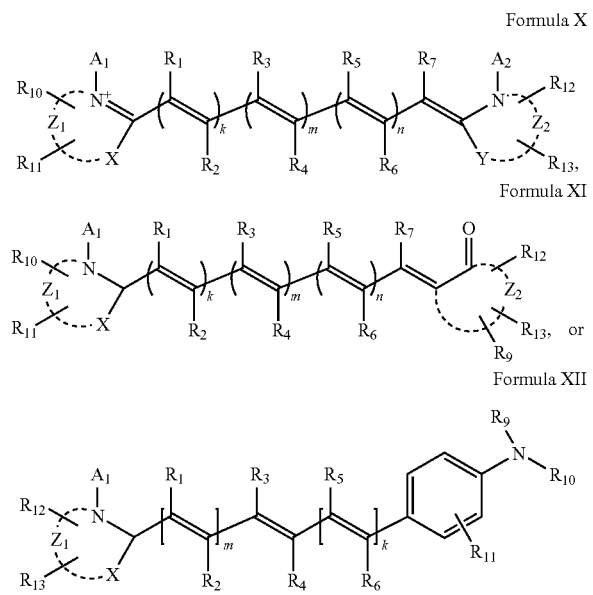

Formula X

Formula XI

Formula XII b) instructions for its use as a chromogen, a fluorochrome, or both,
c) optionally at least one enzyme,
d) optionally at least one co-factor to the enzyme.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

SHORT DESCRIPTION OF DRAWINGS

Figure 8:
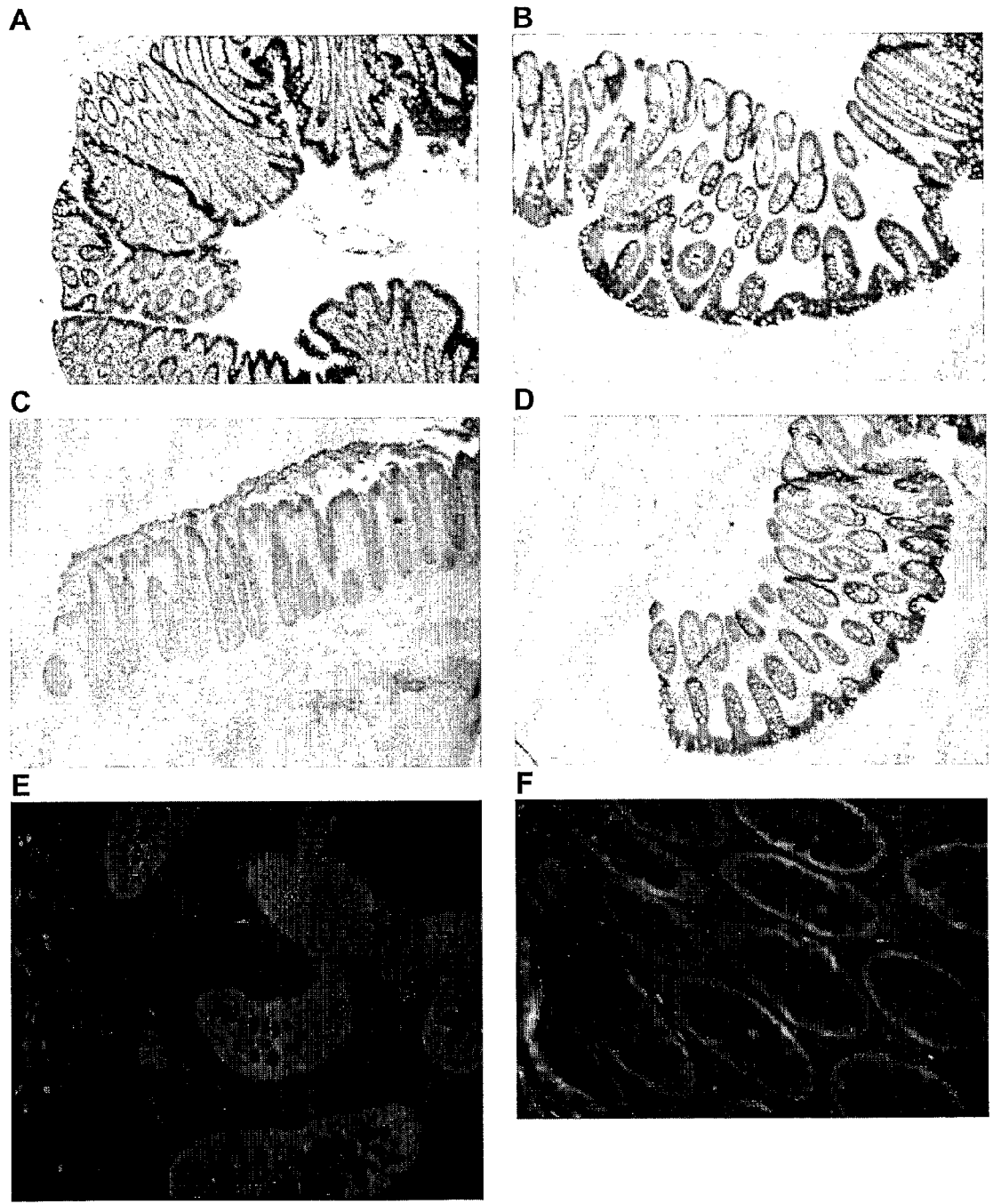

FIG. 8a-f shows colon tissue stained with anti-cytokeratin and detected with cyanine compounds according to the invention. The compounds are visualized either by light microscopy or fluorescent microscopy. FIG. 8a shows a reference where AEC (3-amino-9-ethylecarbazole) is used as a chromogen, FIG. 8b depicts the use of compound IIIa as a chromogen and where the counterstain is Nuclear Fast red, FIG. 8c depicts the use of Compound VII as chromogen and where the counterstain is Nuclear Fast red., FIG. 8d depicts the use of compound IVa as a chromogen, FIG. 8e depict the use of compound IIIb as a precipitated fluorochrome and where DAPI is used as a counterstain, and FIG. 8f depict the use of compound IVa as a precipitated fluorochrome and where DAPI is used as a counterstain.

Figure 9:
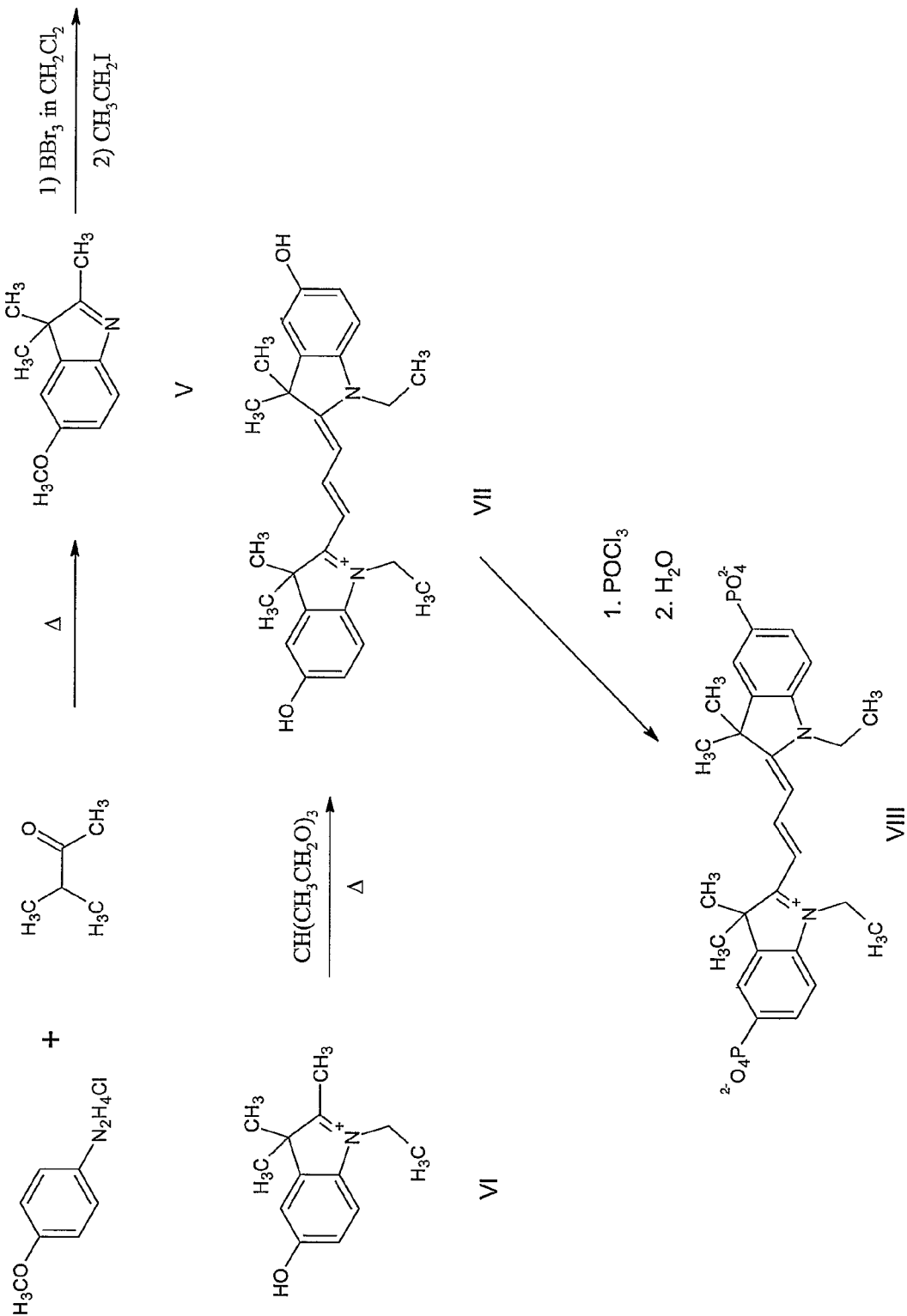

FIG. 9 shows the synthesis of compound VII and an example of how it may be converted to a substrate for Alkaline phosphatase. First, a mixture of 3-Methyl-2-Butanon and 4-Methoxyphenylhydrazine hydrochloride in ethanol is refluxed to give 5-Methoxy-2,3,3-trimethylindolenine (V). Cleavage of the methoxy ether by treatment with Boron tribromide followed by quaternization with ethyliodide yields 1-Ethyl-5-Hydroxy-2,3,3-trimethyl-3H-indolium iodide (VI). Reaction with triethylortho format yields the Cyanine compound (VII). This compound may then further be phosphorylated with phosphoroxytrichloride followed by addition of water to give the bis phosphorylated compound (VIII).

Figure 10:
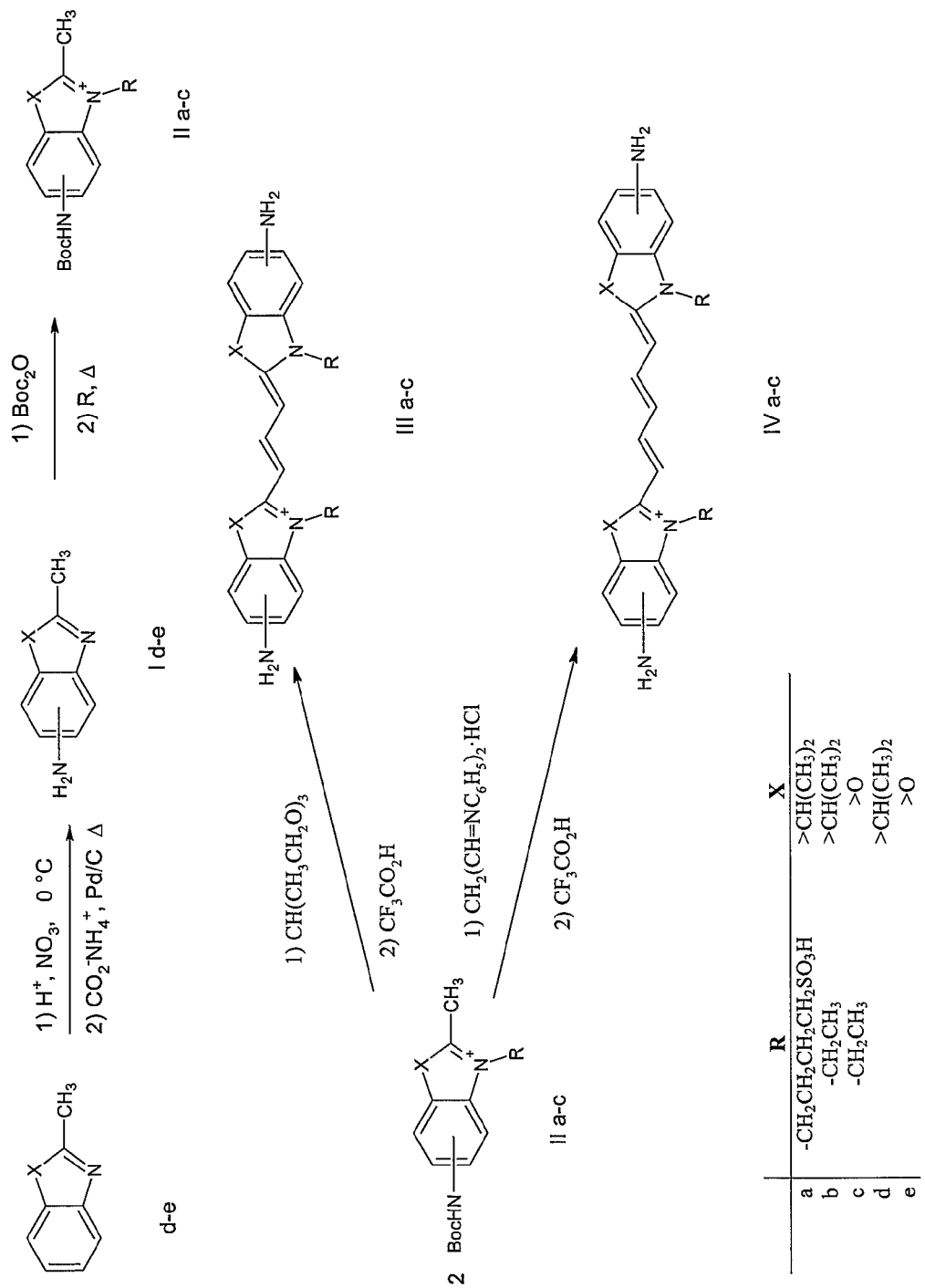

FIG. 10 shows a general scheme for the synthesis of a range of cyanine compounds, such as compound VII, III and IV. First, the starting ring system is nitrated, the nitro group is then reduced to an amino group using ammonium formiate and Palladium on Carbon. The amino group is protected by reaction with di-tertbutyl-di carbonate. Next, the ring nitrogen is quaternized by reaction with an ethyl iodide (R) or butanesultone (R) to give compound II. Reaction with either triethylorthoformiate or malonaldehyde bis(phenylimine) monohydrochloride in both cases followed by treatment with trifluoroacetic acid gives the cyanine compounds III or IV.

Alternatives for X and R in the figure are shown as a-e in the table at the lower left corner of FIG. 10 (below the general synthesis).

Figure 11:
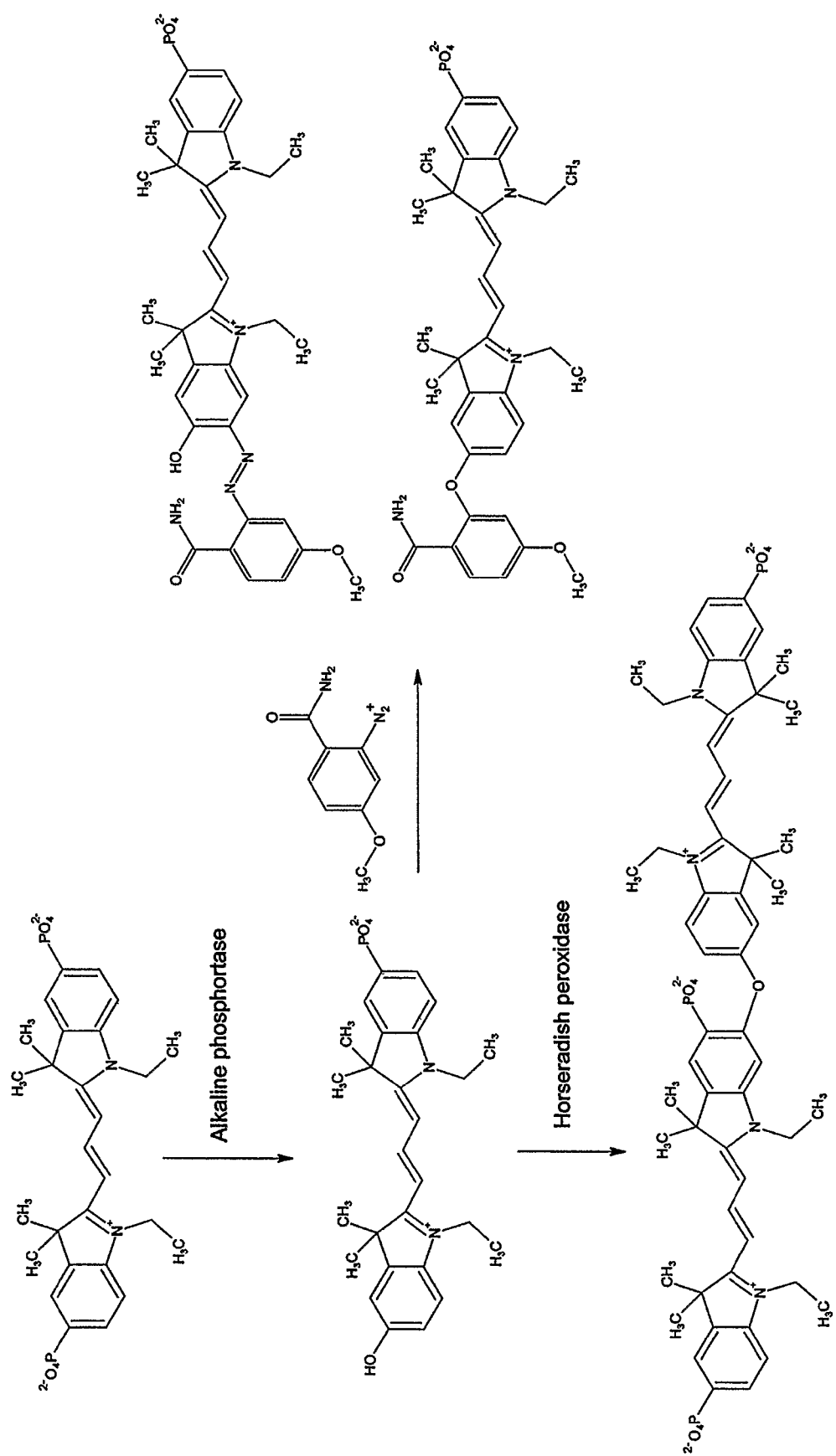

FIG. 11 shows one example of a double, sequential enzymatic processing of a compound. The phosphate group is first hydrolyzed by the AP enzyme, leaving a hydroxyl group available and ready for processing by the HRP enzyme.

DETAILED DESCRIPTION

Definitions

As used herein the term "chromogen" intends to mean a substance, which may be transformed or processed into a pigment. Chromogens form colored precipitates when processed by an enzyme. Under normal conditions of use said precipitates are intensely colored when viewed using ordinary lighting conditions.

The term "carbon atom ring" as used herein refers to a cyclic system of atoms that holds the number of carbon atoms mentioned in the text in addition to other atoms such as nitrogen and sulfur atoms. One example is the indole ring system that consist of 2 fused rings namely a 6 carbon atom ring and a 4 carbon atom ring. The 4 carbon atom ring also has a nitrogen atom included in the ring.

The term "functional group" as used herein refers to a specific atom or groups of atoms that will give a compound a specific chemical characteristic.

The term "color" as used herein refers to any color generated and/or detectable from a chromogen, e.g. a chromogen color, a fluorochroms fluorescens, e.g. a fluorochrome color, or a compound according to the invention.

The term "co-factor" as used herein refers to a compounds needed by an enzyme to process another compound (i.e. hydrogen peroxide needed by HRP) or a compounds that reacts directly with a compound after the enzyme has processed it (i.e. diazonium salt as used for known AP substrates).

The term "precipitates" as used herein refers to a compound or substance that settles out of solution or becomes covalently attached to a molecule. The attachment covalently may be to another molecule in solution, thereby bringing the substance or compound out of solution, or to a tissue molecule, or to any other molecule attached to a tissue or a cell, thereby bringing the substance or compound out of solution.

The term "fluorochrome" refers to a fluorescent substance or compound, wherein said substance or compound precipitates when processed by an enzyme.

The term "aromatic" is herein intended to mean an organic molecule or compound in which the constituent atoms, or any part of them, form a ring. The ring contains at least on carbon-carbon double bond (—CH═CH—). Thus, e.g. an aromatic amine is an amine in which the nitrogen is connected to an aromatic ring.

The Compounds

As revealed above the invention discloses compounds that may be used as chromogens, as fluorochromes, or as both, i.e. the compound has both characteristics. Examples of groups of molecules are cyanine compounds modified for the purpose, e.g. Cy2, Cy3, Cy5, Cy7, merocyanines and styryls. The compounds according to the invention are depicted in the general Formulas X-XII shown in FIG. 1-3.

Furthermore, the compounds may be changed to modify the absorbance and emission to suit specific needs of the user, while retaining the overall structure of the molecule. Said compound may then be tailored to the desired absorption or emit the desired wavelength by simply changing the substituents on the ring systems, or the length of the methine bridge, or both. The overall compound is still the same and as a consequence the optimization of the enzymatic reaction conditions is not necessary.

Thus, the compounds according to the invention are both excellent fluorochromes and excellent chromogens.

Figure 1:
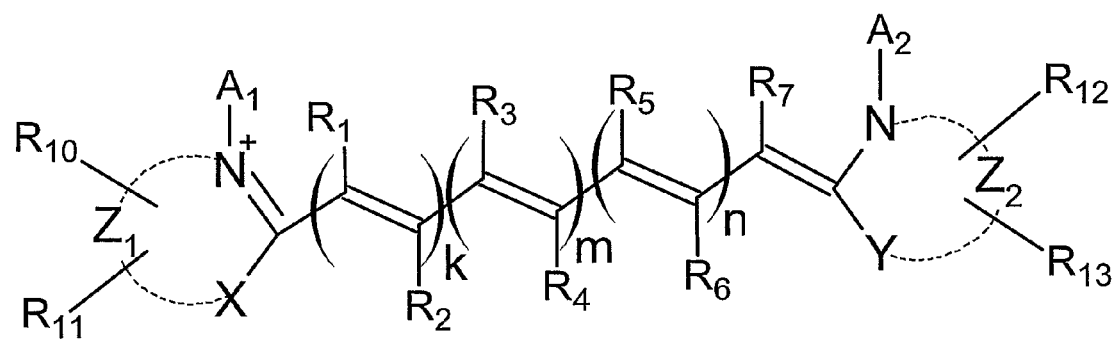
FIG. 1 depicts general Formula X of cyanine based compounds according to the invention.
Figure 2:
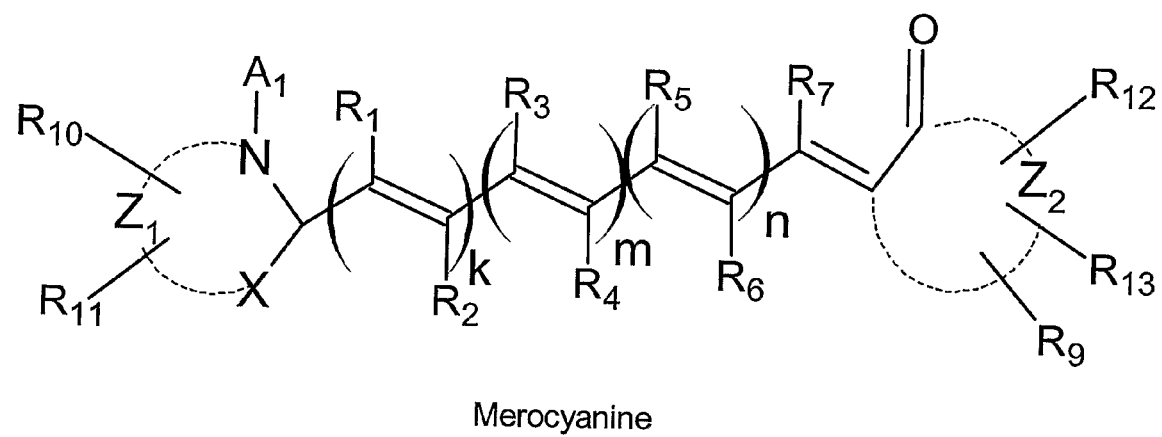
FIG. 2 depicts general Formula XI of merocyanine based compounds according to the invention.
Figure 3:
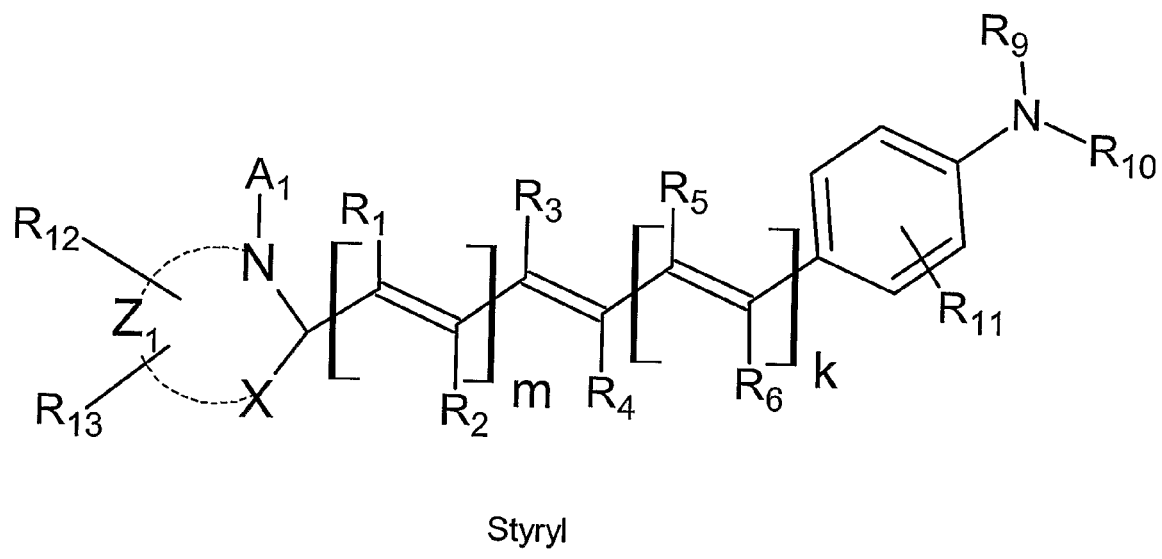
FIG. 3 depicts general Formula XII of styryl based compounds according to the invention.

FIG. 1-3 shows the general formula X, XI and XII of compounds according to the invention. Formula X is cyanine based, Formula is XI merocyanine based, and Formula XII is styryl based.

Thus, the invention provides a compound selected from the group consisting of cyanine, merocyanine, and styryl according to the formulas X-XII and wherein dotted lines $Z_1$ and $Z_2$ represents the atoms necessary to complete the structure selected from the groups consisting of one ring, two fused rings, and three fused rings each said ring having 3 or 4 or 5 or 6 carbon atoms and wherein at least one of said rings has at least one aromatic amine group (—$NH_2$), or at least one aromatic hydroxyl group (—OH), or at least one aromatic phosphate group (—$PO_4$), or a mixture thereof, attached, k and m and n are independently 1 or 0, $R_1$ through $R_{13}$ are individually selected from the group consisting of -(D) and —(B)i-(D)j, X and Y can independently be oxygen, sulfur, selenium, —C($CH_3$)$_2$—, or —CH═CH—, $A_1$ and $A_2$ are selected from the group consisting of -(D)j and —(B)i-(D)j.

Some embodiments are where i and j independently are any numeral between 0-6, such as 0, 1, 2, 3, 4, 5, 6.

In some embodiment, i is 1.

In some further embodiments, j is 1.

In still further embodiments i is 1 and j is 1.

In further embodiments B is a linker. The linker may be of the general formula [—B—]$_n$ and where n is an integer of between 1-10. The linker may be selected from the group consisting of branched alkyl chains of 1-20 carbon atoms, such as 1, 2, 3, 4, 5, 6, 7, 8, 9, 10, 11, 12, 13, 14, 15, 16, 17, 18, 19, or even 20 carbon atoms, straight alkyl chains of 1-20 carbon atoms, such as 1, 2, 3, 4, 5, 6, 7, 8, 9, 10, 11, 12, 13, 14, 15, 16, 17, 18, 19, or even 20 carbon atoms, monoethers containing from 2-20 carbon atoms, such as such as 2, 3, 4, 5, 6, 7, 8, 9, 10, 11, 12, 13, 14, 15, 16, 17, 18, 19, or even 20 carbon atoms, polyethers containing from 2-20 carbon atoms, such as 2, 3, 4, 5, 6, 7, 8, 9, 10, 11, 12, 13, 14, 15, 16, 17, 18, 19, or even 20 carbon atoms, and polymethine chains containing from 1 to 6 carbon atoms, such as 1, 2, 3, 4, 5, or even 6 carbon atoms; and optionally B can connect two of the groups $A_1$, $A_2$, and $R_{1-7}$ thus forming an additional ring system between two of $A_1$, $A_2$, and $R_{1-7}$ making the central methine chain part of a ring system.

In further embodiments D is a group conferring desired properties.

In further embodiments the additional ring system above is a 4-6 carbon atom ring, such as a 4, 5, or even 6 carbon atom ring.

In further embodiments the additional ring system above is a 6 carbon atom ring.

In further embodiments D conferring desired properties is selected from the group consisting of i. neutral groups that reduce water solubility, e.g. hydrogen and halogen atoms, ii. polar groups that increase water solubility e.g. amide sulfonate, sulphate, phosphate quaternary ammonium, hydroxyl and phosphonate, iii. electron donating and withdrawing groups that shift the absorption and emission wavelengths of the molecule, e.g. cyano, acyl aldehyde and alkyl, iv. functional groups e.g. amino, hydroxyl, sulfhydryl carboxyl or carbonyl, and
v. groups that are substrate for an enzyme selected from the group of phosphate, hydroxyl and amino groups, and
vi. a mixture thereof.

The compound will work as a substrate for an enzyme, e.g. horse radish peroxidase (HRP) or alkaline phosphatase (AP). The amino group and the hydroxyl group will make the compound susceptible to HRP processing and the phosphate group will make the compound susceptible for AP. Thus, in further embodiments, —OH, —NH$_2$, and —PO$_4$ are substrates for enzymes. Examples of enzymes are HRP and AP.

In one embodiment the compound comprises at least one aromatic amino group.

In further embodiments the compound comprises 1, 2, 3, 4, 5, 6, 7, 8, 9, or even 10 amino group(s). Further embodiments comprise 2-4 aromatic amino groups. One specific embodiment comprises 4 aromatic amino groups.

In a further embodiment, the compound comprises at least one hydroxyl group.

In further embodiments the compound comprises 1, 2, 3, 4, 5, 6, 7, 8, 9, or even 10, aromatic hydroxyl group(s). Further embodiments comprise 1-2 aromatic hydroxyl group(s). One specific embodiment comprises 2 aromatic hydroxyl groups In still a further embodiment, the compound comprises at least one phosphate group.

In further embodiments the compound comprises 1, 2, 3, 4, 5, 6, 7, 8, 9, or even 10, aromatic phosphate group(s). Further embodiments comprises 1-2 aromatic phosphate group(s). One specific embodiment comprises 2 aromatic phosphate groups.

In still a further embodiment, the compound comprises at least one aromatic phosphate group and at least one aromatic amino group to allow enzyme processing by choice, either by HRP processing, AP processing or processing by both enzymes subsequently or together.

In still a further embodiment, a compound according to the invention comprises at least one phosphate group. The phosphate group is first hydrolyzed by the AP enzyme, leaving a hydroxyl group available and ready for processing by the HRP enzyme if so desired. This embodiment may create two sequential enzyme targets and allow for different enzyme processing in one single compound, i.e. a dual enzyme reaction. This dual enzyme reaction may in specific embodiments be sequential. Furthermore a diazonium salt is not needed to localize the compound in this embodiment since this will be done by the HRP processing step. In this embodiment both enzymes targets are required to be present in the sample to get the localization of the compound. In one embodiment the targets are e.g. Protein1 and Protein 2. These two proteins may, if they are close and if they have affinity for each other, form a hetero dimer comprising of one of each of the proteins. The two proteins may also be separately located from each other, thus not forming a dimer or hetero dimer, but still be close enough for a dual enzyme reaction described below with both AP and HRP to take place. Treating a sample that comprises e.g. the hetero dimer with one Alkaline phosphatase labeled antibody against Protein 1 and a HRP labeled antibody against Protein 2 can then produce a specific stain that shows the dimer is present. The visualization is done with the use of only one dye that will sequentially work as a substrate for the two enzymes. First the anti-Protein 1 AP processes the substrate/dye thereby generating an aromatic hydroxyl group on the dye/substrate. Then the anti-Protein 2 HRP can process the aromatic hydroxyl group on the substrate/dye to give a detectable precipitate. One example of a double enzyme processing step is viewed in FIG. 11. Upon contact with the enzyme the dye will become localized around the enzyme by precipitation, including covalent attachment or localization to nearby molecules. Co-factors for the enzyme are e.g. hydrogen peroxide or a diazonium salt. Diazonium salt will further capture the compound after cleavage of the phosphate group. The compound then forms a colored precipitate that is visible by microscopy, both light and fluorescence.

The delocalization of a pair of electrons on an indole ring across the polymethine unsaturated bridge system defines the absorption maximum that corresponds to the transition from a ground state to an exited state. For every double bond increase in the methine chain, there would be a 100 nm bathochromic shift as opposed to only 20 nm for every additional aromic ring. (Wellington P., Medarova Z., and Moore A., *Synthesis and application of a water soluble near infrared dye for cancer detection using optical imaging.* Bioconjugate Chem., 2005. 16: p. 735-740). Therefore the absorption and emission wavelength of the cyanine compounds can be tuned over a wide range of wavelengths to give the precipitate the desired color. Using the same principle of wavelength tuning the merocyanine and the styryl based compounds absorption can be tuned to the desired wavelength. Examples of calculations for tuning the wavelength can be found in Tyutyulkov, N., et al., *Polymethine dyes: Structure and properties.* 1st ed. 1991: St. Kliment Ohridski University press. 249. The tuning of the compounds is of special importance in the case were more than one compound is to be used on the same slide (multi staining). The absorbance of the compound may then be tuned to provide optimal spectral separation of the absorbance from that of other compounds. Likewise the dyes may be tuned for optimal performance in a scanner with a specific filter set.

In further embodiments, the enzyme is conjugated to a binding molecule capable of binding to at least one target of interest. This is further described below.

In a further embodiment, the at least one enzyme is HRP.

In a further embodiment, the at least one enzyme is AP.

In a further embodiment, the at least one enzyme is at least two enzymes. Examples of at least two enzymes are HRP and AP. In a further embodiment, the at least two enzymes are used in a sequential order being first AP, followed by HRP.

Figure 4:
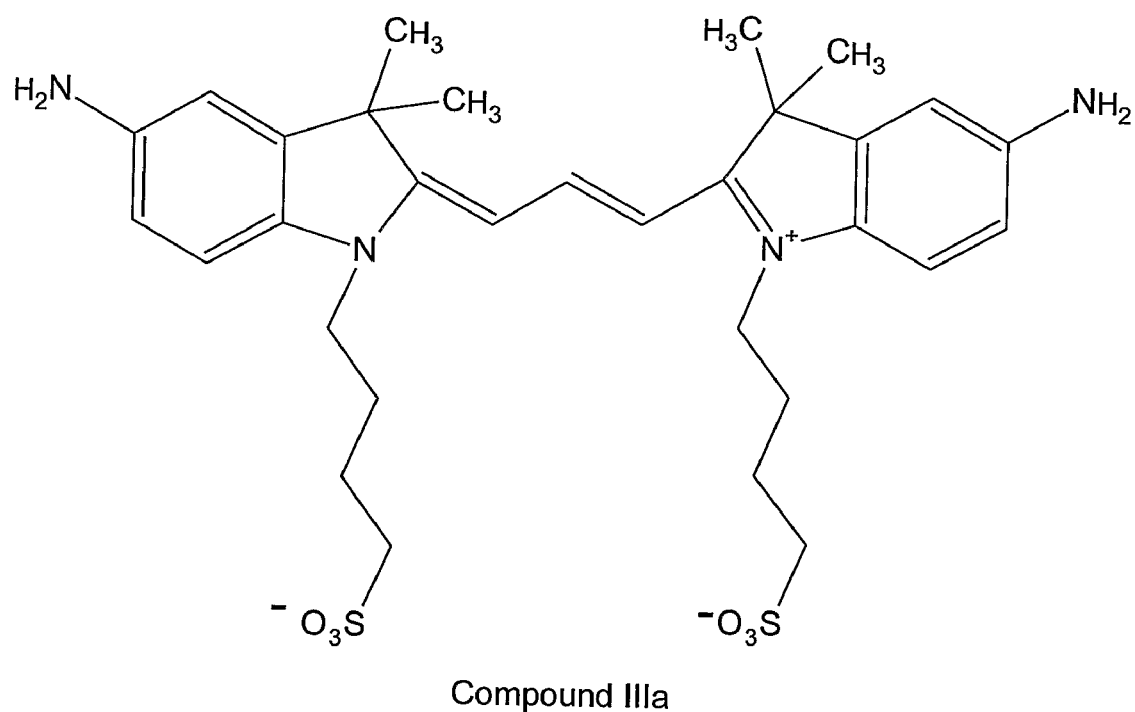
FIG. 4 depicts a compound according to the invention, compound IIIa, that works both as a chromogen and a fluorochrom.

One embodiment of a compound according to the invention is compound IIIa. In compound IIIa, $R_{10}$ and $R_{12}$ is an amino group and defined as a -D. $R_1$, $R_2$, $R_7$, $R_{11}$ and $R_{13}$ is hydrogen and defined as -D. $Z_1$ and $Z_2$ are 6 atoms creating two fused rings, namely a 4 carbon ring with one nitrogen atom and a 6 carbon ring. This specific ring system is the indole ring system. Furthermore, k=1; m=0; and n=0. This embodiment further comprises X as —C(CH$_3$)$_2$— and Y as —C(CH$_3$)$_2$—. Even further, in this embodiment $A_1$ and $A_2$ is —(B)i-(D)j where B is a straight alkyl chain of 4 carbon atoms and D is a sulfonate. Compound IIIa is shown in FIG. 4. Furthermore, in this embodiment, j=1; i=1.

Figure 5:
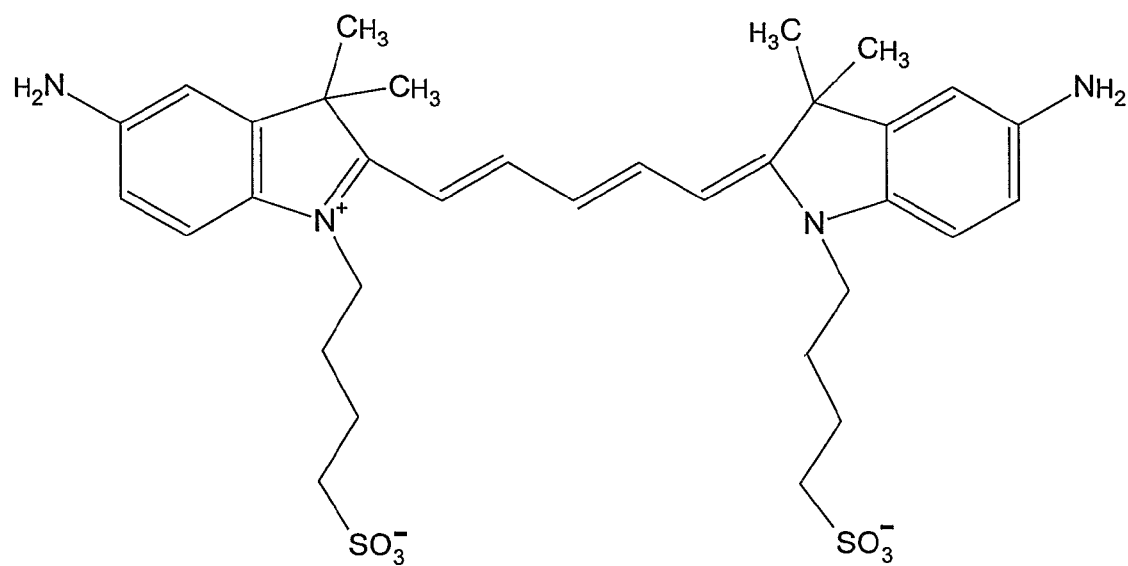
FIG. 5 depicts a compound according to the invention, compound IVa, that works both as a chromogen and a fluorochrom.

A further embodiment of a compound according to the invention is compound IVa. In compound IVa, $R_{10}$ and $R_{12}$ is an amino group and defined as -D, $R_1$, $R_2$, $R_3$, $R_4$, $R_7$, $R_{11}$ and $R_{13}$ is hydrogen and defined as -D. $Z_1$ and $Z_2$ are 6 atoms creating two fused rings, namely a 4 carbon ring with one nitrogen atom and a 6 carbon ring. This specific ring system is the indole ring system. Furthermore, k=1; m=1; n=0. This embodiment further comprises X as —C(CH$_3$)$_2$— and Y as —C(CH$_3$)$_2$—. Even further in this embodiment, $A_1$ and $A_2$ is —(B)i-(D)j where B is a straight alkyl chain of 4 carbon atoms and D is a sulfonate. Compound IVa is shown in FIG. 5. Furthermore, in this embodiment j=1; and i=1.

Figure 6:
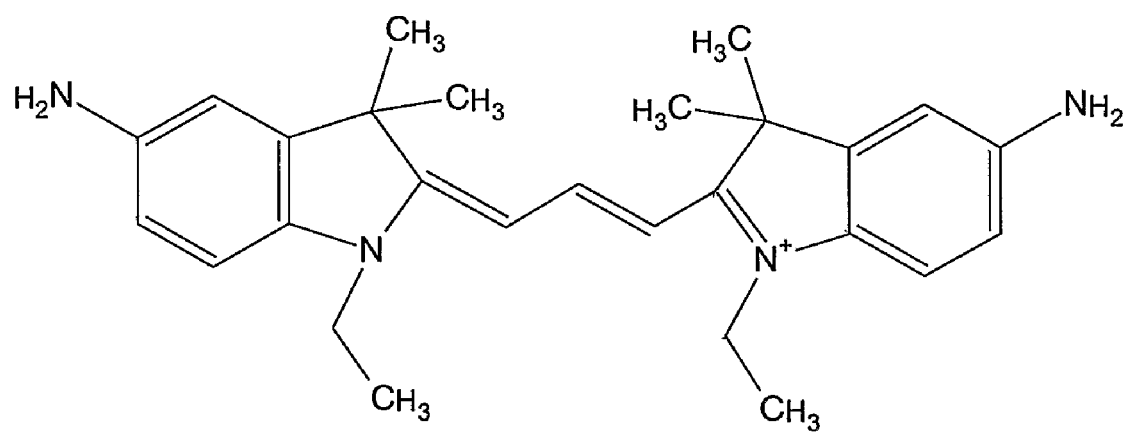
FIG. 6 depicts a compound according to the invention, compound IIIb, that works both as a chromogen and a fluorochrom.

A further embodiment of a compound according to the invention is compound IIIb. In compound IIIb, $R_{10}$ and $R_{12}$ is an amino group and defined as -D, $R_1$, $R_2$, $R_7$, $R_{11}$ and $R_{13}$ is hydrogen and defined as -D. $Z_1$ and $Z_2$ are 6 atoms creating two fused rings, namely a 4 carbon ring with one nitrogen atom and a 6 carbon ring. This specific ring system is the indole ring system. Furthermore, k=1; m=0; n=0. This embodiment further comprises X as —C(CH$_3$)$_2$— and Y as —C(CH$_3$)$_2$—. Even further in this embodiment A$_1$ and A$_2$ is —(B)i-(D)j where B is a straight alkyl chain of 2 carbon atoms and D is hydrogen. Compound IIIb is shown in FIG. 6. Furthermore, in this embodiment, j=1; and i=1.

Figure 7:
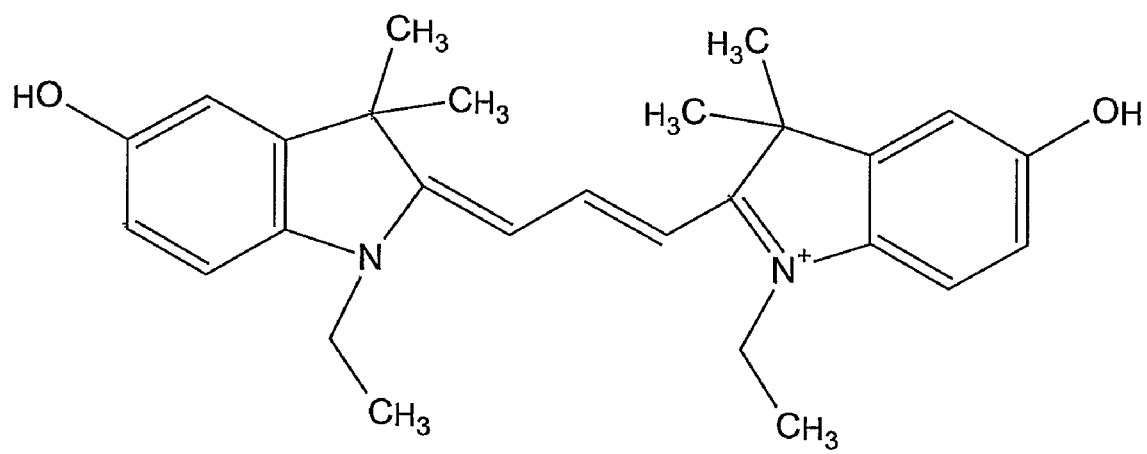
FIG. 7 depicts a compound according to the invention, compound VII, that works both as a chromogen and a fluorochrom.

A further embodiment of a compound according to the invention is compound VII. In compound VII, $R_{10}$ and $R_{12}$ is a hydroxyl group and defined as -D, $R_1$, $R_2$, $R_7$, $R_{11}$ and $R_{13}$ is hydrogen and defined as -D. $Z_1$ and $Z_2$ are 6 atoms creating two fused rings, namely a 4 carbon ring with one nitrogen atom and a 6 carbon ring. This specific ring system is the indole ring system. Furthermore, k=1; m=0; n=0. This embodiment further comprises, X as —C(CH$_3$)$_2$— and Y as —C(CH$_3$)$_2$—. Even further in this embodiment, A$_1$ and A$_2$ is —(B)i-(D)j where B is a straight alkyl chain of 2 carbon atoms and D is hydrogen. Compound VII is shown in FIG. 7. Furthermore, in this embodiment, j=1; and i=1.

Use of Compounds According to the Invention as Chromogens

The invention further discloses several uses of a compound according to the invention as described and exemplified above, selected from the group consisting of cyanine, merocyanine, and styryl according to the general formulas X-XII shown in FIG. 1-3, respectively.

The compound according to the invention has the capacity to work as a chromogen dye. The invention thus discloses the use of a compound according to the invention as a chromogen.

The compound according to the invention further has the capacity to work as a fluorochrome. The invention thus discloses the use of a compound according to the invention as a fluorochrome.

In a further embodiment the compound according to the invention works both as a chromogen and a fluorochrome. Since the compound according to the invention has the capacity to work both as a fluorochrome and as a chromogen it will be up to the end user what properties to use, depending on the assay conditions in each case. This will give a maximal freedom and optimization possibilities when designing an assay.

The compound according to the invention has the capacity to work as a substrate for an enzyme. Upon contact with the enzyme the compound will become fixed around the enzyme by precipitation, meaning that the compound settles out of solution or becomes covalently attached to a molecule. The attachment covalently may be to another molecule in solution, thereby bringing the substance and compound out of solution. This can be a separate reaction between a cofactor or any other molecule and the enzyme processed compound, i.e. no enzyme is required for this reaction Alternatively, the attachment covalently may be to a tissue molecule, or to any other molecule attached to a tissue or a cell, thereby bringing the substance or compound out of solution.

In further embodiments, the at least one enzyme is capable of processing an aromatic amine group (—NH$_2$), an aromatic hydroxyl group (—OH), or an aromatic phosphate group (—PO$_4$).

The compound will thereby upon contact with the enzyme as described above form a colored precipitate that is visible by microscopy, in this case light microscopy when used as a chromogen according to known and available procedures for light microscopy when analyzing a chromogenic dye. However, the compound is visible as a fluorochrome as well by visualization in a fluorescence microscope, according to known and available procedures for fluorescence microscopy.

The above use of the compound may be in e.g. histochemistry, immunohistochemistry, cytochemistry, immunocytochemistry, ELISA (enzyme linked immunosorbent assay), ISH (in situ hybridization) or FISH (fluorescent in situ hybridization) or CISH (chromogen in situ hybridization), and e.g. flow cytometry, or in any other method utilizing either chromogenic color(s) or fluorescens colour(s), or both. Such methods are known and described in the art in e.g. Johnstone A P, Turner M W eds *Immunochemistry 2. A practical approach*, Oxford university press 1997, pg 71-130; R. A. DeLellis, *Advances in Immunohistochemistry*, Raven Press, N.Y., 1988, ISBN 0-88167-394-3; J. C. Jennette, *Immunology in diagnostic pathology*, CRC Press, 1989, U.S., ISBN 0-8493-4987-7; T. Boenisch, *Handbook in Immunological Staining Methods* (DakoCytomation A/S, 2001, CA); Sambrok, J. et al., *Molecular Cloning: A Laboratory Manual*, Second Edition, (1989); Crowther, *Enzyme-Linked Immunosorbent Assay (ELISA)*, in *Molecular Biomethods Handbook*; Rapley et al. [eds.], pp. 595-617, Humana Press, Inc., Totowa, N.J. [1998]; Harlow and Lane (eds.), *Antibodies: A Laboratory Manual*, Cold Spring Harbor Laboratory Press [1988]; Ausubel et al. (eds.), *Current Protocols in Molecular Biology*, Ch. 11, John Wiley & Sons, Inc., New York [1994]; Jaroszeski et al., *Method in Molecular Biology*, (1998), Vol 9 1: Flow Cytometry Protocols, Hummama Press; Longobanti Givan, (1992) *Flow Cytometry*, First Principles, Wiley Liss. Further examples of suitable protocols for the compounds according to the invention are found in the Example section.

As mentioned above the compound further has the capacity to work as a substrate for an enzyme. The processing of a chromogenic dye or compound by an enzyme to form a colored precipitate is known in the art and fully applicable in this system. Examples of enzymes that will have the capacity to process compounds according to the invention are Horse radish peroxidase (HRP), Alkaline phosphtase (AP), or any other enzyme utilizing —OH, —NH$_2$, or PO$_4$ as a substrate (Kemeny, D. M. 1997. Enzyme-linked immunoassays. In Immunochemistry 1—A Practical Approach. Johnstone, A. P. and Turner, M. W. (Eds) IRL Press. pp. 147-175).

Most enzymes require co-factors to work. Examples of co-factors for some of the enzymes mentioned above are hydrogen peroxidase. Horse radish peroxidase catalyses the breakdown of hydrogen peroxide. This reaction can be coupled to the oxidation of a chromogenic compound such as the compounds according to the invention.

Alkaline phosphatase is an enzyme that catalyses the cleavage of inorganic phosphate non-specifically from a wide variety of phosphate esters.

For AP the presence of a diazonium salt to react with the hydroxyl group after the cleavage of the phosphate is required. Alternatively the by AP processed substrate, i.e. the compounds according to the invention, can be precipitated by further processing by HRP.

The compounds according to the invention may be substrates for HRP, AP, or both. Compounds comprising an aromatic amino group (—NH$_2$) or aromatic hydroxyl group (—OH) may work as a substrate for HRP. Compounds comprising an aromatic phosphate group (—PO$_4$) may work as a substrate for AP.

In one embodiment the compound according to the invention is a substrate for both HRP and AP. In said embodiment AP may process said compound according to the invention comprising an aromatic phosphate group (—PO$_4$). The processing by AP may then be followed by a processing of the compound by HRP, as the AP processing may generate an aromatic hydroxyl group (—OH) after the (—PO₄) processing.

Further uses of the compound according to the invention as mentioned above are as a fluorochrome. The compound according to the invention has the capacity to work as a fluorochrome. A fluorochrome is fluorescent when appropriately excited. A fluorochrome will fluoresce, i.e. produce or exhibit fluorescence, when irradiated with light of the appropriate wavelength.

In still a further embodiment, the compound is a precipitating fluorochrome, i.e. has the capacity to form a solid that settles out of solution.

In even further embodiments, the precipitating fluorochrome is also a chromogen. Thus, the compound may be designed to suit specific needs of the user by simply changing the substituents on the ring system, by adjusting and varying the length of the polymethin chain, or by choice of A₁ and A₂. Examples of substituents are given above.

Thus, the precipitating compounds according to the invention are both excellent fluorochromes and excellent chromogens. This double capacity is further exemplified below.

Methods for Precipitating the Compound

Disclosed herein are methods for precipitating a compound according to the invention, e.g. a compound according to formula X-XII shown in FIG. 1-3. As mentioned above, the processing of a chromogen is well known in the art. The compounds according to the invention may be processed either with HRP, AP, or both, depending on the substituent groups on the aromatic rings.

The method comprises the steps of
a) providing said compound according to formula

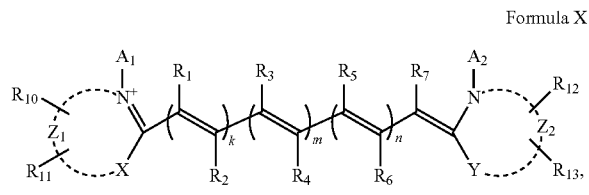

Formula X

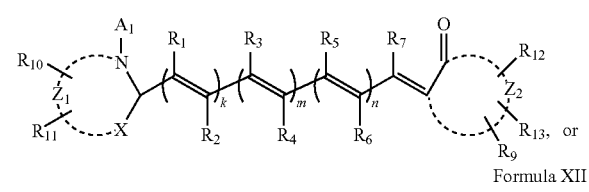

Formula XI

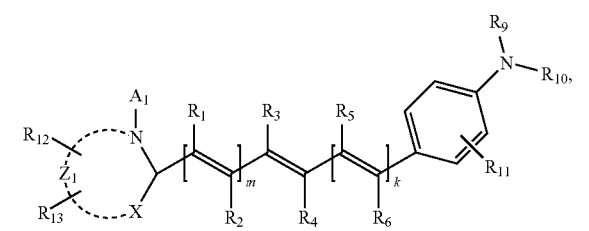

Formula XII b) providing an enzyme,
c) contacting the compound according to the invention with said enzyme,
d) optionally providing a co-factor,
wherein said compound forms a precipitate.

In further embodiments of the method, the enzyme is capable of processing an aromatic amine group (—NH₂), an aromatic hydroxyl group (—OH), or an aromatic phosphate group (—PO₄).

Further embodiments are wherein the enzyme is conjugated to a binding molecule capable of binding to at least one target of interest.

Further embodiments are wherein the compound is provided as a solution in water or in N-methylpyrrolidone (NMP). In further embodiments, the compound may be provided in a stock solution to be diluted upon use, in e.g. a buffer, for a ready-to-use-dilution buffer of the compounds (e.g. a 2-component kit).

In further embodiments the compound comprises at least one aromatic amine group, aromatic hydroxyl group, or aromatic phosphate group. Furthermore embodiments of the compounds are wherein
  dotted lines $Z_1$ and $Z_2$ represents the atoms necessary to complete the structure selected one ring two fused rings, and three fused rings each said ring having 3 or 4 or 5 or 6 carbon atoms and wherein at least one of said rings has at least one aromatic amine group, at least one aromatic hydroxyl group, at least one aromatic phosphate group, or a mixture thereof, attached,
  k and m and n are independently 1 or 0,
  $R_1$ through $R_{13}$ are individually selected from the group consisting of -D and —(B)i-(D)j,
  X and Y can independently be Oxygen, Sulfur, Selenium, —C(CH₃)₂—, or —CH=CH—,
  $A_1$ and $A_2$ are selected from the group consisting of -D and —(B)i-(D)j.

Where the compound will be fixed to or around the enzyme upon contact, it will form a precipitate or become covalently attached to a molecule, thereby forming a precipitate. The attachment covalently may be to another molecule in solution, thereby bringing the substance and compound out of solution, or to a tissue molecule, or to any other molecule attached to a tissue or a cell, thereby bringing the substance or compound out of solution.

Some embodiments are where i and j independently are any numeral between 0-6, such as 0, 1, 2, 3, 4, 5, 6.

In some embodiments, i is 1.

In some further embodiments, j is 1.

In still further embodiment i is 1 and j is 1.

In further embodiments B is a linker.

In further embodiments, B is of the general formula —[B]ᵢ—, and wherein o is an integer of between 1-10, such as 1, 2, 3, 4, 5, 6, 7, 8, 9, or even 10. In one embodiment, o is 1-3. In another embodiment, o is 1.

In further embodiments, B is selected from the group consisting of branched alkyl chains of 1-20 carbon atoms, such as 1, 2, 3, 4, 5, 6, 7, 8, 9, 10, 11, 12, 13, 14, 15, 16, 17, 18, 19, or even 20 carbon atoms, straight alkyl chains of 1-20 carbon atoms, such as 1, 2, 3, 4, 5, 6, 7, 8, 9, 10, 11, 12, 13, 14, 15, 16, 17, 18, 19, or even 20 carbon atoms, monoethers containing from 2-20 carbon atoms, such as such as 2, 3, 4, 5, 6, 7, 8, 9, 10, 11, 12, 13, 14, 15, 16, 17, 18, 19, or even 20 carbon atoms, polyethers containing from 2-20 carbon atoms, such as 2, 3, 4, 5, 6, 7, 8, 9, 10, 11, 12, 13, 14, 15, 16, 17, 18, 19, or even 20 carbon atoms, and polymethine chains containing from 1 to 6 carbon atoms, such as 1, 2, 3, 4, 5, or even 6 carbon atoms; optionally B can connect two of the groups $A_1$, $A_2$, and $R_{1-7}$ thus forming an additional ring system between two of $A_1$, $A_2$, and $R_{1-7}$ making the central methine chain part of a ring system.

In further embodiments the additional ring system above are 4-6 carbon atom rings, such as 4, 5, or even a 6 carbon atom ring.

In further embodiments the additional ring system above are 6 carbon atom rings.

In further embodiments, D is a group conferring desired properties.

In further embodiments, D conferring desired properties is selected from the group consisting of
i. neutral groups that reduce water solubility selected from the group consisting of hydrogen and halogen atoms,
ii. polar groups that increase water solubility selected from the group of amide sulfonate, sulphate, phosphate quaternary ammonium, hydroxyl and phosphonate,
iii. electron donating and withdrawing groups that shift the absorption and emission wavelengths of the molecule,
iv. functional groups selected from the group consisting of amino, hydroxyl, sulfhydryl carboxyl or carbonyl,
v. groups that are substrate for an enzyme selected from the group of phosphate hydroxyl and amino, and
vi. a mixture thereof.

In further embodiments, said enzyme is HRP or AP.

Further embodiments are wherein the compound is the compound according to IIIa in FIG. 4, the compound according to IVa in FIG. 5, the compound according to IIIb in FIG. 6, or the compound according to VII in FIG. 7.

The compound thus forms a coloured precipitate. The precipitate is formed to, around or close to the enzyme as mentioned above.

In further embodiments, the method further comprises detecting the precipitate.

In further embodiments, the precipitate is detected by visualization by microscopy, e.g. light microscopy, fluorescence microscopy or both according to procedures known in the art.

The detection may be manual or in an automated method, e.g. an automated scanning method. Even further embodiments are wherein the microscopy is by an automatic procedure, e.g. by an automatic scanning procedure. Example of such systems are ACIS® technology platforms (Clarient, US). Further examples of automated scanning methods as well as automated sample processing are given in U.S. Pat. No. 6,352,861, U.S. Pat. No. 5,839,091, U.S. Pat. No. 6,183, 693, U.S. Pat. No. 5,948,359, U.S. Pat. No. 5,839,091, WO04059441A2, WO04059297A1, WO04059288A2, WO04059287A2, WO04059284A2, WO04058950A1, WO04058404A2, WO04057308A1, WO04057307A1, all incorporated herein by reference.

In one embodiment the automated method comprises a method of automated sample processing that may comprise one or more steps of:
establishing an automated sample processing system having an automated process operation capability that causes automated process operation events through robotic sample process functions;
loading a plurality of carriers with biologic samples in the automated sample processing system;
loading or accessing data enabling the sample processing system to define at least one protocol for the control of the sample processing of each of the loaded samples; and
Optionally performing the sample processing using at least one vibrator element to enhance the processing under at least one processing step.

A further embodiment of an automated sample processing method may comprise one or more steps of:
establishing an automated sample processing system having an automated process operation capability that causes automated process operation events through robotic sample process functions;
loading a plurality carriers with biologic samples in the automated sample processing system;
loading or accessing data enabling the sample processing system to define at least one protocol for the control of the sample processing of each of the loaded samples; and
performing the sample processing using at least one "tapping or knocking" element to enhance the processing under at least one processing step.

Further embodiments may relate to e.g. automated control systems for sample processing and may also be directed to data acquisition, input, maintenance, and retrieval for sample processing, as well as information sharing of processing protocol and processing information, and real-time or adaptive capabilities for processing.

Still even further embodiments include wherein systems and methods may comprise optionally an automated sample processing system comprising a plurality of drawers, a plurality of sample carrier elements that may even be each removably configured with one of the drawers, and an adaptive or other sample processing control system. The drawers and sample carriers may be both movable and removable. The sample processing control system may automate the sample processing system such that one or more samples may be processed according to one or more protocols, potentially indicated by information on slides or otherwise input to the system. This sample processing may comprise one or more sampling protocols and steps, such as de-paraffinization, target retrieval, and staining.

Furthermore, a sensor may be provided, in some embodiments that may automatically identify information from one or more samples, sample carriers, or slides. In embodiments, protocol information may be provided or made available by the sample processing control system. The sample processing system may then process one or more samples or perhaps slides, or one or more batches of slides, concurrently, sequentially, or in any other temporal fashion, potentially in accordance with protocol information previously provided for a sample by a user or other decision maker. This information may then be made available for use by the sample processing control system. Sample batches or individual slides may even be inserted or removed during processing protocol steps by the control and monitoring accomplished by the adaptive sample processing control system.

Methods for Detecting a Target

The invention further comprises a method for detecting a target. The method comprises the steps of providing at least one compound according to formula X-XII according to the invention, providing at least one enzyme, contacting the compound according to the invention with the enzyme, optionally providing a co-factor, where the compound will be fixed to, around or close to the enzyme upon contact by precipitation thereby forming a precipitate, detecting said precipitate either by visual light or fluorescence, wherein detection of said precipitate is a direct or indirect detection of said target.

In further embodiments the enzyme is conjugated to a binding molecule binding directly or indirectly to a target of interest.

In further embodiments, the enzyme is capable of processing an aromatic amine group ($-NH_2$), an aromatic hydroxyl group ($-OH$), or an aromatic phosphate group ($-PO_4$).

In further embodiments, the precipitate is detected by microscopy, e.g. light microscopy or fluorescence microscopy. Both techniques are known in the art.

Examples of targets are any biological or non-biological target.

Biological targets refer to any defined and non-defined biological particles, such as, but not limited to, macromolecular complexes, including viruses, cells, tissues and combinations, that are produced as a result of biological reactions in cells.

Non-biological targets refer to molecules or structures that are made outside of cells as a result of either human or non-human activity.

Non-limiting examples of biological targets are cells, proteins, peptides, cytokines, antibodies enzymes, hormones, lymphokines, lipids, phospholipids, receptors, antigens, haptenes, lectines, toxins, carbon hydrates, oligosaccharides, polysaccharides, nucleic acids, deoxyribonucleic acids (DNA), ribonucleic acids (RNA), PNA (peptide nucleic acid), derivatized deoxyribonucleic acid, derivatized nucleic acids, derivatized ribonucleic acids, derivatized PNA, DNA-fragments, RNA-fragments, PNA fragments, virus particles, virus components, yeast, yeast components, bacteria, bacteria components, blood cells, blood cell components, biologic cells, etc.

Non-limiting examples of non-biological targets are drugs, non-cellular blood components, poisons, polymers, polymer particles, glass particles, glass surfaces, plastic surfaces, plastic particles, polymer membranes, and metals.

Further non-limiting examples of targets are chemically defined targets and chemically non-defined targets. "Chemically defined targets" refer to those targets with known chemical nature and/or composition; "chemically non-defined targets" refer to targets that have either unknown or partially known chemical nature/composition.

Non-limiting examples of binding molecules binding to targets are e.g. protein, peptides, antibodies including parts and fragments thereof, nucleic acids, deoxyribonucleic acids (DNA), ribonucleic acids (RNA), PNA (peptide nucleic acid), derivatized deoxyribonucleic acid, derivatized nucleic acids, derivatized PNA, derivatized ribonucleic acids, DNA-fragments, RNA-fragments, as well as PNA fragments.

Synthesis of the Compounds According to the Invention

The present invention further provides synthesis of compounds according to the invention.

FIG. 9 shows the synthesis of compound VII and an example of how it may be converted to a substrate for Alkaline phosphatase (AP). First, a mixture of 3-Methyl-2-Butanon and 4-Methoxyphenylhydrazine hydrochloride in ethanol is refluxed to give 5-Methoxy-2,3,3-trimethylindolenine (V). Cleavage of the methoxy ether by treatment with Boron tribromide followed by quaternization with ethyliodide yields 1-Ethyl-5-Hydroxy-2,3,3-trimethyl-3H-indolium iodide (VI). Reaction with triethylortho format yields the Cyanine compound (VII). This compound may then further be phosphorylated with phosphoroxytrichloride followed by water hydrolysis to give the bis phosphorylated compound (VIII).

FIG. 10 shows a general scheme for the synthesis of a range of cyanine compounds. First, the starting ring system is nitrated, the nitro group is then reduced to an amino group using ammonium formiate and Palladium on Carbon. The amino group is protected by reaction with di-tertbutyl-di carbonate. Next the ring nitrogen is quaternized by reaction with an ethyl iodide (R) or butanesultone (R) to give compound II. Reaction with either triethylorthoformiate or malonaldehyde bis(phenylimine) monohydrochloride in both cases followed by treatment with trifluoroacetic acid gives the cyanine compounds III or IV A general overview of the synthesis is given in FIGS. 9 and 10. The methods used are described in Mujumdar, R. B., et al. (*Cyanine dye labeling reagents containing isothiocyanate groups*. Cytometry, 1989. 10(1): p. 11-19) and in Noland, W. E., L. R. Smith, and K. R. Rush (*Nitration of indoles III Polynitration of 2-alkylindoles*. Journal of the American Chemical Society, 1965. 30: p. 3457-3469) except for some exceptions given in example 1 below. Compound V and VI are made according to Shragina L (Liquid Crystals, 1990, Vol 7, No 5, pg 643-655) except for the quarternization of the nitrogen in VI where ethyl iodide was used instead of methyl iodide. General guides to the synthesis of the compounds depicted in Formula X, Formula XI and Formula XII can be found in Tyutyulkov, N., et al., *Polymethine dyes: Structure and properties*. 1st ed. 1991: St. Kliment Ohridski University press. 249. and in U.S. Pat. No. 5,486,616 and U.S. Pat. No. 6,686,145 B1.

A Kit

The invention further discloses a kit according to the invention. The kit comprises a) at least one compound according to the invention. Such compounds are according to the formula

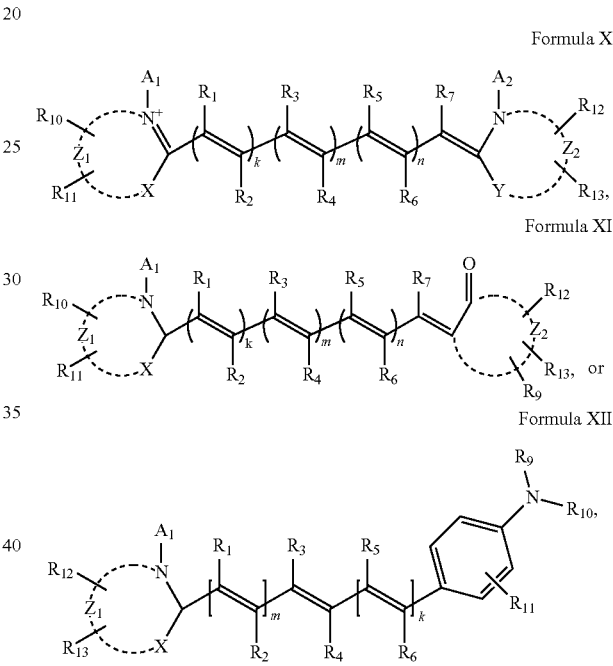

Formula X

Formula XI

Formula XII b) instructions for its use as a chromogen, a fluorochrome, or both, c) optionally at least one enzyme, d) optionally at least one co-factor to the enzyme.

Multistaining kits, e.g. kits comprising compounds for staining several biological markers in a sample is further disclosed. The localization of several stained markers in combination allows more valuable information than from single marker stains to be extracted. Thus, the present invention discloses such multistaining kits comprising compounds according to the invention.

Further embodiments are wherein the kit comprises 1, 2, 3, 4, 5, 6, 7, 8, 9, 10, 15, or even 20 or more compounds according to the invention.

Even further embodiments are wherein the kit comprises, 2-5, e.g. 2-3, or 4-5 compounds according to the invention.

Further embodiments are wherein the instructions are to perform a method for detecting a target according to any of the methods disclosed according to the invention.

Further embodiments are wherein said enzyme is capable of processing an aromatic amine group (—$NH_2$), an aromatic hydroxyl group (—OH), or an aromatic phosphate group (—$PO_4$).

Further embodiments are wherein the enzyme is conjugated to a binding molecule binding to at least one target of interest. Examples are given above.

Further embodiments are wherein in the formula X-XII
dotted lines $Z_1$ and $Z_2$ represents the atoms necessary to complete the formula selected from the groups consisting of one ring, two fused rings, and three fused rings each said ring having 3 or 4 or 5 or 6 carbon atoms and wherein at least one of said rings has at least one aromatic amine group (—$NH_2$), or at least one aromatic hydroxyl group (—OH), or at least one aromatic phosphate group (—$PO_4$), or a mixture thereof, attached, k and m and n are independently 1 or 0, $R_1$ through $R_{13}$ are individually selected from the group consisting of -D and —(B)i-(D)j, X and Y can independently be Oxygen, Sulfur, Selenium, —$C(CH_3)_2$—, or —CH=CH—, and $A_1$ and $A_2$ are selected from the group consisting of -D and —(B)i-(D)j.

Some embodiments are where i and j independently are any numeral between 0-6, such as 0, 1, 2, 3, 4, 5, 6.

In some embodiments, i is 1.

In some further embodiments, j is 1.

In still further embodiments i is 1 and j is 1.

Further embodiments are wherein B is a linker.

Further embodiments are wherein B is of the general formula —[B]$_o$—, and where o is an integer of between 1-10, such as 1, 2, 3, 4, 5, 6, 7, 8, 9, or even 10. In one embodiment, o is 1-3. In another embodiment, o is 1.

Further embodiments are wherein B is selected from the group consisting of branched alkyl chains of 1-20 carbon atoms, such as 1, 2, 3, 4, 5, 6, 7, 8, 9, 10, 11, 12, 13, 14, 15, 16, 17, 18, 19, or even 20 carbon atoms, straight alkyl chains of 1-20 carbon atoms, such as 1, 2, 3, 4, 5, 6, 7, 8, 9, 10, 11, 12, 13, 14, 15, 16, 17, 18, 19, or even 20 carbon atoms, monoethers containing from 2-20 carbon atoms, such as such as 2, 3, 4, 5, 6, 7, 8, 9, 10, 11, 12, 13, 14, 15, 16, 17, 18, 19, or even 20 carbon atoms, polyethers containing from 2-20 carbon atoms, such as 2, 3, 4, 5, 6, 7, 8, 9, 10, 11, 12, 13, 14, 15, 16, 17, 18, 19, or even 20 carbon atoms, and polymethine chains containing from 1 to 6 carbon atoms, such as 1, 2, 3, 4, 5, or even 6 carbon atoms; and optionally B can connect two of the groups $A_1$, $A_2$, and $R_{1-7}$ thus forming an additional ring system between two of $A_1$, $A_2$, and $R_{1-7}$ thereby making the central methine chain part of a ring system.

Further embodiments are wherein D is a group conferring desired properties.

Further embodiments are wherein the additional ring system is a 4-6 carbon atom ring, such as 4, 5, or even a 6 carbon atom ring.

Further embodiments are wherein the additional ring system is a 6 carbon atom ring.

Further embodiments are wherein D conferring desired properties is selected from the group consisting of
i. a neutral group that reduce water solubility,
ii. a polar group that increase water solubility,
iii. an electron donating group,
iv. an electron withdrawing group,
v. a functional group,
vi. a group that is substrate for an enzyme, and wherein said group is selected from the group consisting of a phosphate group, an hydroxyl group, and an amino group, and
vii. a mixture thereof.

Further embodiments are wherein said enzyme is horse radish peroxidase (HRP), or alkaline phosphatase (AP).

Further embodiments are wherein the compound is [formula IIIa].

Further embodiments are wherein the compound is [formula IVa].

Further embodiments are wherein the compound is [formula IIIb].

Further embodiments are wherein the compound is [formula VII].

It is further specifically contemplated that any embodiment of any compound, method, kit or use may be used with respect to any other embodiment of said compound, method, kit or use according to the invention.

EXAMPLES

Example 1

Synthesis of Compounds According to the Invention

The objective with this example is to describe the method of synthesis of compound IIIa, IVb, IIIb, V and VI.

The synthesis is outlined in FIG. 10.

Compound IIIa, IVb, and IIIb

Compound IIIa, IVb, and IIIb can be made following procedures for cyanine dyes as previously described in the literature (*Nitration of indoles III Polynitration of 2-alkylindoles*. Journal of the American Chemical Society, 1965. 30: p. 3457-3469); Mujumdar R. B., Cytometry, 10:11-19, 1989) with the following exceptions and modifications given below.

5-amino-2,3,3 trimethyl-(3H)-indole 5-amino-2,3,3 trimethyl-(3H)-indole was synthesized as follows:

10.15 g of 5-nitro-2,3,3 trimethyl-(3H)-indole (50 mmol) was suspended in 150 ml methanol.

16.6 g ammoniumformiat followed by 380 mg 10% Pd/C is added.

Reflux for 3½ hours.

Filter through sea sand and remove the methanol on rotor vapour.

Partition the residue between 200 mL of dichlormethane and 200 mL of water. The water phase is extracted 2 times with dichlormethane.

Evaporate the combined organic phases to get the crude product.

Recrystallize from heptane.

Yield: 4.06 g (46.9%)

In some cases the Boc protected compounds were purified by silica gel chromatography using methanol in dichlormethane. Likewise compound VII was purified on a silica gel column before use.

The Boc protection groups were removed according to the following general procedure:

1 mmol Boc protected compound was dissolved in 8 mL methanol. 24 mL of trifluoroacetic acid was added. After 1 hour the compound is precipitated by the addition of 400 mL diethylether. The compound was collected by filtration and dried in an exicator. Yield approx: 0.5 mmol.

Compound V and VI

Compounds V and VI were made as described in the literature (Shragina L., et al., *Searching for photochromic liquid crystals spironaphthoxazine substituted with a mesogenic group*. Liquid crystals, 1990, 7(5): p. 643-655) except for the quaternization of the nitrogen in VI were ethyl iodide was used instead of methyl. Compound VII was made from compound VI following the procedures described for making III from II.

Example 2

Procedure for IHC Staining of Tissues on Slides

The objective of this example is to describe a general procedure for staining of paraffin embedded tissue. In this example a cytokeratin antibody on a multiblock containing tissue from breast, colon, kidney and tonsil was used. The counterstaining is optional since its only purpose is to make examination of the tissue easy for the person looking at it. The peroxidase blocking is only needed if the tissue examined contains proteins with peroxidase activity.

| Procedure | |
|---|---|
| 1. Xylen wash | 2 × 5 min. |
| 2. 96% ethanol wash | 2 × 2 min. |
| 3. 70% ethanol wash | 2 × 2 min. |
| 4. Water wash | 1 × 1 min. |
| 5. Antigenretrival<br>Boil for 10 min using microwave or<br>40 min at 95° C. in a water bath<br>(DakoCytomation S 1700) | 1 × 48 min. |
| 6. Cool to room temerature | 20 min. |
| 7. Water wash | 30 sec. |
| 8. Wash (Dakocytomation S 1968) | 5 min. |
| 9. Peroxidase blocking (optional) | 5 min. |
| 10. Wash (Dakocytomation S 1968) | 5 min. |
| 11. Anti-cytokeratin incubation (Dakocytomation N 1590) | 30 min. |
| 12. Wash (Dakocytomation S 1968) | 5 min. |
| 13. Envision + (Dakocytomation K5007) | 30 min |
| 14. Wash (Dakocytomation S 1968) | 5 min. |
| 15. Incubate in dye solution (1.5 nmol/mL or 1 mg compound/ml in Chemate substrate buffer from DakoCytomation K5007) | 10 min. |
| 16. Water | 5 min. |
| 17. Counterstain (DakoCytomation S1963) (optional) | 3 min. |
| 18. Water | 5 min |
| 19. Mount | |

DakoCytomation products:
S 1700. Target retrival solution
S 1968. Tris buffered saline (TBS) pH 7.6
N 1590 Monoclonal mouse anti-Human cytokeratin clone AE1/AE3, ready-to-use.
K5007 ChemMate™ Envision™ Detection kit, Peroxidase/DAB Rabbit/mouse. Only the Envision reagent of this kit was used as the enzyme substrate, the diaminobenzidine component was not used. The compound solution were used in the place of diaminobenzidine component)

Example 3

Staining of Paraffin Embedded Colon Tissue

The objective of this example is to demonstrate that compounds according to formula X can be used as a chromogen.
Stock solutions of the compounds in N-methylpyrrolidon (20-30 mg/mL) were kept at 5° C. For staining these stock solutions were diluted into the Chemate substrate buffer of kits obtained from Dakocytomation code # K5007. The final concentration used was 0.5 mg/mL for chromogen use and 10 µg/mL for fluorescens applications
Staining procedure was according to Example 2. Colon tissue stained with anti-cytokeratin and visualized for light microscopy or fluorescens microscopy with different cyanine compounds are shown in FIG. 8a-f. FIG. 8a shows a reference where AEC (3-amino-9-ethylecarbazole) is used as the chromogen. FIG. 8b depicts the use of Compound IIIa as a chromogen where the counterstain is Nuclear Fast red. FIG. 8c depicts the use of Compound VII as chromogen. The counterstain is Nuclear Fast red. FIG. 8d depicts the use of compound IVa as a chromogen. FIG. 8e depicts the use of compound IIIb as a precipitated fluorochrome. The counterstain is DAPI. FIG. 8f shows the use of compound IVa as a precipitated fluorochrome and where DAPI is used as a counterstain.

Example 4

Procedure for Staining Tissue for Fluorescence Microscopy

The objective of this example is to describe a general procedure for staining tissue for fluorescence microscopy.

| Procedure | |
|---|---|
| 1. Xylen wash | 2 × 5 min. |
| 2. 96% ethanol wash | 2 × 2 min. |
| 3. 70% ethanol wash | 2 × 2 min. |
| 4. Water wash | 1 × 1 min. |
| 5. Antigenretrival<br>Boil for 10 min using microwave or<br>40 min at 95° C. in a water bath<br>(DakoCytomation S 1700) | 1 × 48 min. |
| 6. Cool to room temperature | 20 min. |
| 7. Water wash | 30 sec. |
| 8. Wash (Dakocytomation S 1968) | 5 min. |
| 9. Peroxidase blocking (optional) | 5 min. |
| 10. Wash (Dakocytomation S 1968) | 5 min. |
| 11. Anti-cytokeratin incubation (Dakocytomation N 1590) | 30 min. |
| 12. Wash (Dakocytomation S 1968) | 5 min. |
| 13. Envision + (Dakocytomation K5007) | 30 min |
| 14. Wash (Dakocytomation S 1968) | 5 min. |
| 15. Incubate in dye solution (15 nmol/mL or ~10 µg compound/mL in Chemate substrate buffer from DakoCytomation K5007)) | 10 min. |
| 16. Water | 5 min. |

Mount with vector shield containing DAPI

The invention claimed is:

1. A method for precipitating at least one compound of formula:

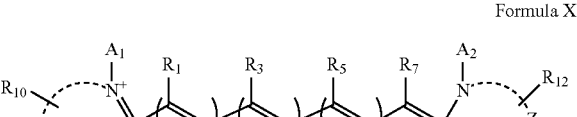

Formula X

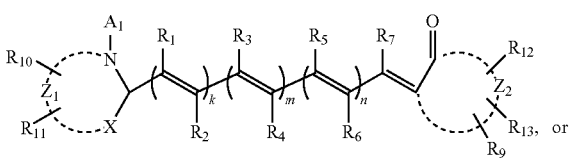

Formula XI

, or

-continued

Formula XII

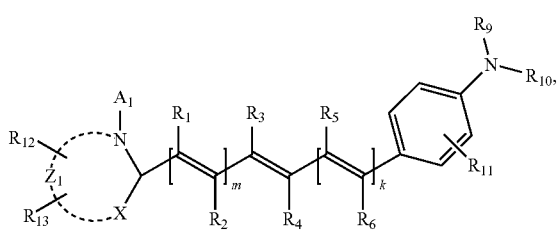

wherein, in said compound:
dotted lines $Z_1$ and $Z_2$ represent the atoms necessary to complete the formula chosen from one ring, two fused rings, and three fused rings, each said ring comprising 3 to 6 carbon atoms wherein at least one of said rings has attached at least one aromatic amine group (—$NH_2$), at least one aromatic hydroxyl group (—OH), at least one aromatic phosphate group (—$PO_4$), or a mixture thereof;
k, m, and n are independently 0 or 1;
X and Y are independently chosen from oxygen, sulfur, selenium, —C($CH_3$)$_2$—, and —CH=CH—; and
$A_1$, $A_2$, and $R_{1-13}$ are independently chosen from -D and —(B)$_i$-(D)$_j$, wherein
D is chosen from:
  i.) a neutral group that reduces water solubility;
  ii.) a polar group that increases water solubility;
  iii.) an electron donating group;
  iv.) an electron withdrawing group;
  v.) a functional group;
  vi.) a group that is a substrate for an enzyme, said group being chosen from a phosphate group, a hydroxyl group and an amino group; and
  vii.) a mixture thereof; and
B is chosen from:
  branched alkyl chains of 1 to 20 carbon atoms:
  straight alkyl chains of 1 to 20 carbon atoms;
  monoethers containing 2 to 20 carbon atoms;
  polyethers containing 2 to 20 carbon atoms; and
  polymethine chains containing 1 to 6 carbon atoms;
wherein i and j are independently integers from 0 to 6;
said method comprising the steps:
  (a) providing said at least one compound;
  (b) providing at least one enzyme;
  (c) contacting said at least one compound with said at least one enzyme; and
  (d) optionally providing at least one co-factor;
wherein said at least one compound forms a precipitate.

2. The method according to claim 1, wherein B is a linker of the general formula —[B]$_n$—, wherein n is an integer from 1 to 10.

3. The method according to claim 1, wherein B connects two of the groups chosen from $A_1$, $A_2$, $R_1$, $R_2$, $R_3$, $R_4$, $R_5$, $R_6$, and $R_7$, forming an additional ring system between said two groups, thereby making the central methine chain part of a ring system.

4. The method according to claim 3, wherein said additional ring system is a 4, 5, or 6 carbon atom ring.

5. The method according to claim 4, wherein said additional ring system is a 6 carbon atom ring.

6. The method according to claim 1, wherein said compound is of Formula X.

7. The method according to claim 1, wherein said compound is of Formula XI.

8. The method according to claim 1, wherein said compound is of Formula XII.

9. The method according to claim 1, wherein said at least one enzyme is capable of processing at least one of an aromatic amine group (—$NH_2$), an aromatic hydroxyl group (—OH), and an aromatic phosphate group (—$PO_4$).

10. The method according to claim 1, wherein said at least one enzyme is horse radish peroxidase (HRP).

11. The method according to claim 1, wherein said at least one enzyme is alkaline phosphatase (AP).

12. The method according to claim 1, wherein said enzyme is two enzymes being alkaline phosphatase (AP) and horse radish peroxidase (HRP).

13. The method according to claim 12, wherein said two enzymes are used in a sequential order being first AP, followed by HRP.

14. The method according to claim 1, wherein said compound and/or its derivative is a substrate for both horse radish peroxidase (HRP) and alkaline phosphatase (AP).

15. The method according to claim 1, wherein said at least one enzyme is conjugated to a binding molecule capable of binding to at least one target of interest.

16. The method according to claim 15, wherein said binding molecule is chosen from proteins, peptides, antibodies, nucleic acids, deoxyribonucleic acid (DNA), ribonucleic acid (RNA), peptide nucleic acid (PNA), and any derivative thereof.

17. The method according to claim 1, further comprising the step of detecting said precipitate.

18. The method according to claim 17, wherein said precipitate is detected by microscopy.

19. The method according to claim 18, wherein the microscopy is light microscopy, fluorescence microscopy, or both.

20. The method according to claim 18, wherein the microscopy is performed manually or by automatic scanning.

21. The method according to claim 1, wherein said method is used in histochemistry, immunohistochemistry, cytochemistry, immunocytochemistry, ELISA (enzyme linked immunosorbent assay), ISH (in situ hybridization), FISH (fluorescent in situ hybridization), CISH (chromogen in situ hybridization), flow cytometry, or in any other method utilizing a chromogenic compound, a fluorescence compound, or both.

22. The method according to claim 1, wherein said at least one compound is chosen from Formula IIIa

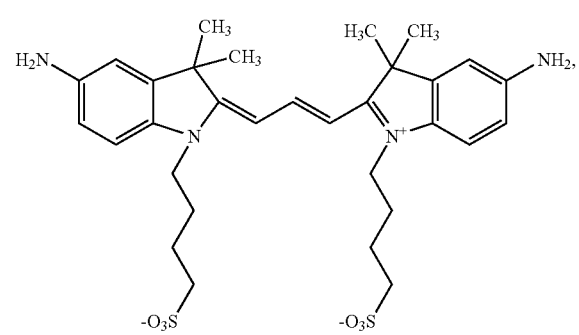

-continued

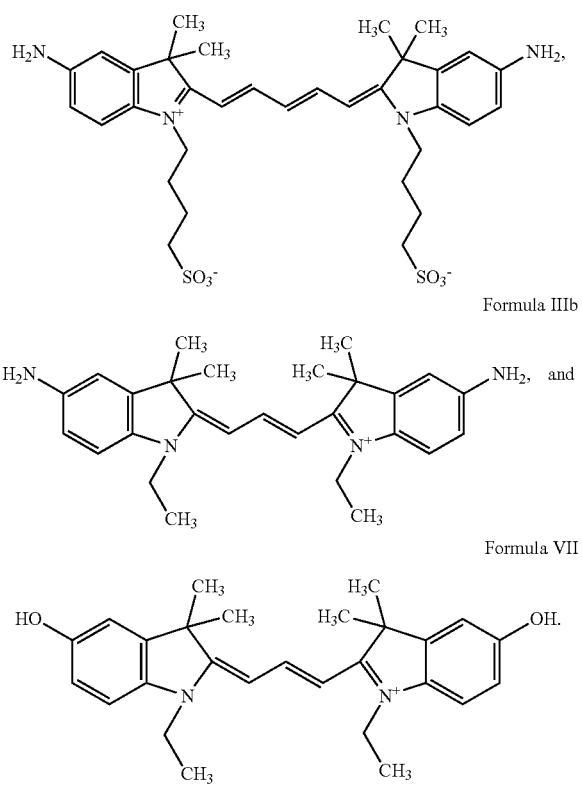

Formula IVa

Formula IIIb

Formula VII

23. The method according to claim 22, wherein said compound is of Formula IIIa.

24. The method according to claim 22, wherein said compound is of Formula IVa.

25. The method according to claim 22, wherein said compound is of Formula IIIb.

26. The method according to claim 22, wherein said compound is of Formula VII.

27. The method according to claim 22, wherein said at least one enzyme is capable of processing at least one of an aromatic amine group (—$NH_2$) and an aromatic hydroxyl group (—OH).

28. The method according to claim 22, wherein said at least one enzyme is conjugated to a binding molecule capable of binding to at least one target of interest.

29. The method according to claim 28, wherein said binding molecule is chosen from proteins, peptides, antibodies, nucleic acids, deoxyribonucleic acid (DNA), ribonucleic acid (RNA), peptide nucleic acid (PNA), and any derivative thereof.

30. The method according to claim 22, wherein said at least one enzyme is horse radish peroxidase (HRP).

31. The method according to claim 22, wherein said method is used in histochemistry, immunohistochemistry, cytochemistry, immunocytochemistry, ELISA (enzyme linked immunosorbent assay), ISH (in situ hybridization), FISH (fluorescent in situ hybridization), CISH (chromogen in situ hybridization), flow cytometry, or in any other method utilizing a chromogenic compound, a fluorescence compound, or both.

32. The method according to claim 22, further comprising the step of detecting said precipitate.

33. The method according to claim 32, wherein said precipitate is detected by microscopy.

34. The method according to claim 32, wherein the microscopy is light microscopy, fluorescence microscopy, or both.

35. The method according to claim 32, wherein the microscopy is performed manually or by automatic scanning.

36. A method for detecting a target comprising the steps:
a.) providing at least one compound chosen from

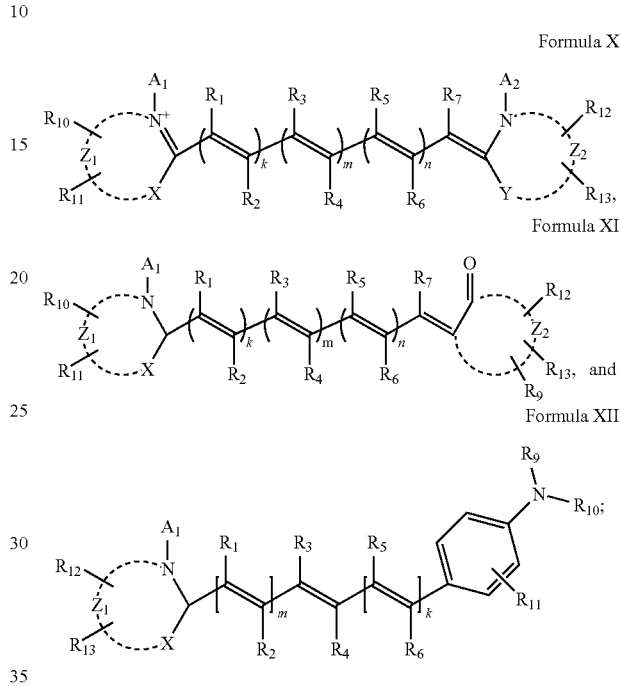

Formula X

Formula XI

Formula XII (b) providing at least one enzyme;
(c) contacting said at least one compound with said at least one enzyme;
(d) optionally providing at least one co-factor; and
(e) detecting the precipitate;
wherein the detection of said precipitate is a direct or indirect detection of said target;
wherein, independently for each said compound:
dotted lines $Z_1$ and $Z_2$ represent the atoms necessary to complete the formula chosen from one ring, two fused rings, and three fused rings, each said ring comprising 3 to 6 carbon atoms wherein at least one of said rings has attached at least one aromatic amine group (—$NH_2$), at least one aromatic hydroxyl group (—OH), at least one aromatic phosphate group (—$PO_4$), or a mixture thereof;
k, m, and n are independently 0 or 1;
X and Y are independently chosen from oxygen, sulfur, selenium, —$C(CH_3)_2$—, and —CH=CH—;
$A_1$, $A_2$, and $R_{1-13}$ are independently chosen from -D and —$(B)_i$-$(D)_j$, wherein
D is chosen from:
i.) a neutral group that reduces water solubility;
ii.) a polar group that increases water solubility;
iii.) an electron donating group;
iv.) an electron withdrawing group;
v.) a functional group;
vi.) a group that is a substrate for an enzyme, said group being chosen from a phosphate group, a hydroxyl group and an amino group; and
vii.) a mixture thereof; and B is chosen from:
  branched alkyl chains of 1 to 20 carbon atoms:
  straight alkyl chains of 1 to 20 carbon atoms;
  monoethers containing 2 to 20 carbon atoms;
  polyethers containing 2 to 20 carbon atoms; and
  polymethine chains containing 1 to 6 carbon atoms;
  wherein i and j are independently integers from 0 to 6.

37. A kit comprising:
(a) at least one compound chosen from:

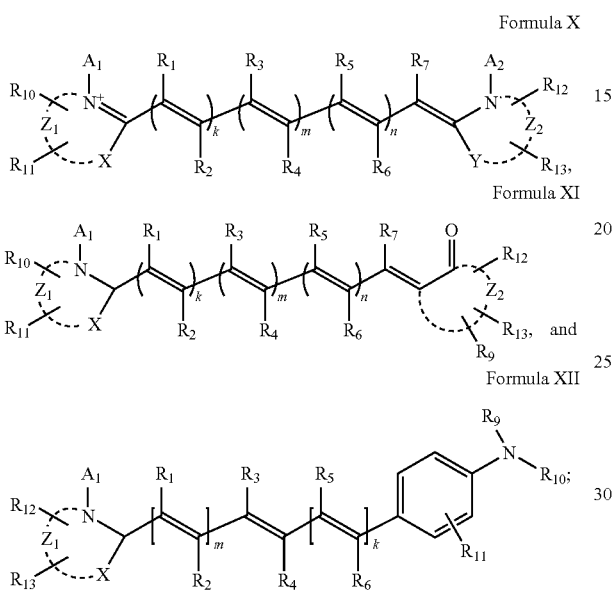

Formula X

Formula XI

Formula XII (b) instructions for use of said at least one compound as a chromogen, a fluorochrome, or both;
(c) optionally at least one enzyme; and
(d) optionally at least one co-factor to the enzyme;
wherein, independently for each said compound:
  dotted lines $Z_1$ and $Z_2$ represent the atoms necessary to complete the formula chosen from one ring, two fused rings, and three fused rings, each said ring comprising 3 to 6 carbon atoms wherein at least one of said rings has attached at least one aromatic amine group (—$NH_2$), at least one aromatic hydroxyl group (—OH), at least one aromatic phosphate group (—$PO_4$), or a mixture thereof;
  k, m, and n are independently 0 or 1;
  X and Y are independently chosen from oxygen, sulfur, selenium, —$C(CH_3)_2$—, and —CH=CH—; and $A_1$, $A_2$, and $R_{1-13}$ are independently chosen from -D and —(B)$_i$-(D)$_j$, wherein
  D is chosen from:
    i.) a neutral group that reduces water solubility;
    ii.) a polar group that increases water solubility;
    iii.) an electron donating group;
    iv.) an electron withdrawing group;
    v.) a functional group;
    vi.) a group that is a substrate for an enzyme, said group being chosen from a phosphate group, a hydroxyl group and an amino group; and
    vii.) a mixture thereof; and
  B is chosen from:
    branched alkyl chains of 1 to 20 carbon atoms:
    straight alkyl chains of 1 to 20 carbon atoms;
    monoethers containing 2 to 20 carbon atoms;
    polyethers containing 2 to 20 carbon atoms; and
    polymethine chains containing 1 to 6 carbon atoms;
  wherein i and j are independently integers from 0 to 6.

38. A compound of Formula IIIa:

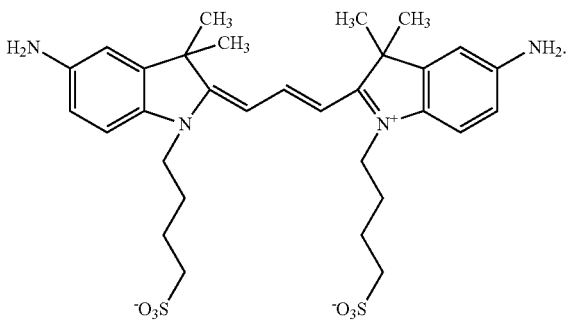

39. A compound of Formula IVa:

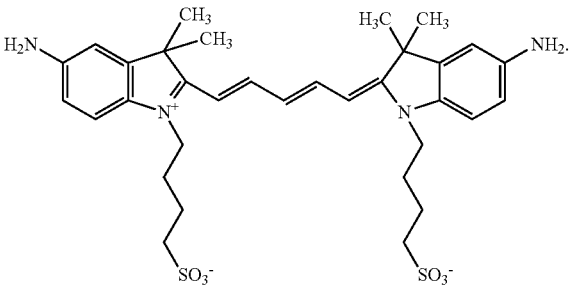

* * * * *